(12) United States Patent
Kugler et al.

(10) Patent No.: US 11,349,084 B2
(45) Date of Patent: May 31, 2022

(54) CHARGE TRANSFER SALTS AND USES THEREOF

(71) Applicants: Cambridge Display Technology Limited, Godmanchester (GB); Sumitomo Chemical Company Limited, Tokyo (JP)

(72) Inventors: Thomas Kugler, Godmanchester (GB); Sheena Zuberi, Godmanchester (GB); Florence Bourcet, Godmanchester (GB)

(73) Assignees: Cambridge Display Technology Limited, Godmanchester (GB); Sumitomo Chemical Company Limited, Tokyo (JP)

( * ) Notice: Subject to any disclaimer, the term of this patent is extended or adjusted under 35 U.S.C. 154(b) by 959 days.

(21) Appl. No.: 16/063,673

(22) PCT Filed: Dec. 16, 2016

(86) PCT No.: PCT/GB2016/053966
§ 371 (c)(1),
(2) Date: Jun. 18, 2018

(87) PCT Pub. No.: WO2017/103609
PCT Pub. Date: Jun. 22, 2017

(65) Prior Publication Data
US 2020/0270394 A1  Aug. 27, 2020
US 2021/0261723 A9  Aug. 26, 2021

(30) Foreign Application Priority Data
Dec. 18, 2015  (GB) .................................... 1522439
Feb. 19, 2016  (GB) .................................... 1602925
(Continued)

(51) Int. Cl.
*H01L 51/00* (2006.01)
*C07D 235/18* (2006.01)
(Continued)

(52) U.S. Cl.
CPC ........ *H01L 51/0072* (2013.01); *C07D 235/18* (2013.01); *C08G 61/02* (2013.01);
(Continued)

(58) Field of Classification Search
None
See application file for complete search history.

(56) References Cited

U.S. PATENT DOCUMENTS 5,179,467 A  1/1993  Buchwalter et al.
8,920,944 B2  12/2014  Limmert et al.
(Continued)

FOREIGN PATENT DOCUMENTS

EP  0 431 547 A  6/1991
EP  1 561 768 A1  8/2005
(Continued)

OTHER PUBLICATIONS

Machine translation of EP 2738194 is attached (Year: 2012).*
(Continued)

*Primary Examiner* — Bilkis Jahan
(74) *Attorney, Agent, or Firm* — Wolf, Greenfield & Sacks, P.C.

(57) ABSTRACT

A charge-transfer salt formed from a material comprising a repeat unit of formula (I) and an n-dopant: wherein BG is a backbone group of the repeat unit; $R^1$ is a ionic substituent comprising at least one cationic or anionic group; n is at least 1; $R^2$ is a non-ionic substituent; and m is 0 or a positive integer; the material further comprising a counterion balancing the charge of the cationic or anionic group.

(Continued)

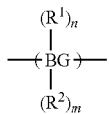

(I)

22 Claims, 9 Drawing Sheets

(30) Foreign Application Priority Data

Feb. 19, 2016 (GB) .................................... 1602928
Jul. 29, 2016 (WO) .............. PCT/GB2016/052347

(51) Int. Cl.
*C08G 61/02* (2006.01)
*H01L 51/50* (2006.01)
*H01L 51/56* (2006.01)

(52) U.S. Cl.
CPC ...... *H01L 51/0039* (2013.01); *H01L 51/0051* (2013.01); *C08G 2261/143* (2013.01); *C08G 2261/148* (2013.01); *C08G 2261/1424* (2013.01); *C08G 2261/1426* (2013.01); *C08G 2261/3142* (2013.01); *C08G 2261/514* (2013.01); *C08G 2261/95* (2013.01); *H01L 51/0007* (2013.01); *H01L 51/0028* (2013.01); *H01L 51/5092* (2013.01); *H01L 51/56* (2013.01); *H01L 2251/308* (2013.01); *H01L 2251/552* (2013.01)

(56) References Cited

U.S. PATENT DOCUMENTS

| | | | |
|---|---|---|---|
| 8,951,646 B2* | 2/2015 | Tanaka | H01L 51/0039 428/690 |
| 9,536,633 B2* | 1/2017 | Higashimura | H01L 21/28 |
| 2011/0006294 A1* | 1/2011 | Tanaka | C08G 61/02 257/40 |
| 2011/0248267 A1 | 10/2011 | Wei et al. | |
| 2012/0256296 A1 | 10/2012 | Wei et al. | |
| 2014/0070178 A1 | 3/2014 | Lee et al. | |

FOREIGN PATENT DOCUMENTS

| | | |
|---|---|---|
| EP | 2 738 194 A1 | 6/2014 |
| GB | 2 513 378 A | 10/2014 |
| JP | H02-169575 A | 6/1990 |
| JP | H02-294009 A | 12/1990 |
| JP | 2004-002703 A | 1/2004 |
| JP | 2004-059899 A | 2/2004 |
| JP | 2006-176755 A | 7/2006 |
| JP | 2012-216811 A | 11/2012 |
| WO | WO 2007/126929 A2 | 11/2007 |
| WO | WO 2008/029155 A2 | 3/2008 |
| WO | WO 2010/088419 A2 | 8/2010 |
| WO | WO 2012/133229 A1 | 10/2012 |
| WO | WO 2013/098648 A1 | 7/2013 |
| WO | WO 2013/122182 A1 | 8/2013 |
| WO | WO 2015/082879 A1 | 6/2015 |

OTHER PUBLICATIONS

Machine translation of GB 2513378 is attached (Year: 2014).*
Machine translation of EP 1561768 is attached (Year: 2003).*
Machine translation of JP2011071197A—Mar. 28, 2011 is attached (Year: 2011).*
PCT/GB2016/052347, Oct. 10, 2016, International Search Report and Written Opinion.
PCT/GB2016/053966, Mar. 6, 2017, International Search Report and Written Opinion.
GB1522439.7, Jul. 29, 2016, Combined Search and Examination Report.
GB1602925.8, Dec. 21, 2016, Combined Search and Examination Report.
GB1602928.2, Dec. 21, 2016, Combined Search and Examination Report.
International Search Report and Written Opinion for International Application No. PCT/GB2016/052347, dated Oct. 10, 2016.
International Search Report and Written Opinion for International Application No. PCT/GB2016/053966, dated Mar. 6, 2017.
Combined Search and Examination Report for British Application No. 1522439.7, dated Jul. 29, 2016.
Combined Search and Examination Report for British Application No. 1602925.8, dated Dec. 21, 2016.
Combined Search and Examination Report for British Application No. 1602928.2, dated Dec. 21, 2016.
[No Author Listed] Database WPI Accession No. 1990-242935. 1990, 6 pages.
[No Author Listed] Database WPI Accession No. 1991-024983. 1991, 6 pages.
Ferraris et al., Performance evaluation of poly 3-(phenylthiophene) derivatives as active materials for electrochemical capacitor applications. Chem Mater. Nov. 1, 1998;10(11):3528-35.
Lin et al., Conjugated copolymers comprised cyanophenyl-substituted spirobifluorene and tricalbazole-triphenylamine repeat units for blue-light-emitting diodes. Journal of Polymer Science Part A: Polymer Chemistry. Dec. 7, 2009;48(2):292-301.
Naab et al., Mechanistic study on the solution-phase n-doping of 1,3-Dimethyl-2-aryl-2,3-dihydro-1 H-benzoimidazole derivatives. Journal of the American Chemical Society. Oct. 9, 2013;135(40):15018-25.
Shi et al., Toward high performance n-type thermoelectric materials by rational modification of BDPPV backbones. J Am Chem Soc. 2015;137:6979-82.
Voortman et al., Stabilizing cations in the backbones of conjugated polymers. J Mater Chem C. Jan. 1, 2014;2(17):3407-15.
Wei et al., Use of a 1 H-benzoimidazole derivative as an n-type dopant and to enable air-stable solution-processed n-channel organic thin-film transistors. J. Am Chem Soc. Jul. 7, 2010;132(26):8852-3.

* cited by examiner

CHARGE TRANSFER SALTS AND USES THEREOF

RELATED APPLICATIONS

This application is a national stage filing under 35 U.S.C. 371 of International Patent Application Serial No. PCT/GB2016/053966, filed Dec. 16, 2016, which is a Box VI priority of International Patent Application Serial No. PCT/GB2016/052347, filed Jul. 29, 2016, and which claims priority to United Kingdom application number GB 1602925.8, filed Feb. 19, 2016, United Kingdom application number GB 1602928.2, filed Feb. 19, 2016, and United Kingdom application number GB 1522439.7, filed Dec. 18, 2015, each of which is incorporated herein by reference in their entirety.

FIELD OF THE INVENTION

The invention relates to n-doped materials, in particular n-doped polymers, methods of forming said n-doped materials and electronic devices containing said n-doped materials.

BACKGROUND OF THE INVENTION

Electronic devices containing active organic materials are attracting increasing attention for use in devices such as organic light emitting diodes (OLEDs), organic photoresponsive devices (in particular organic photovoltaic devices and organic photosensors), organic transistors and memory array devices. Devices containing active organic materials offer benefits such as low weight, low power consumption and flexibility. Moreover, use of soluble organic materials allows use of solution processing in device manufacture, for example inkjet printing or spin-coating.

An organic light-emitting device has a substrate carrying an anode, a cathode and an organic light-emitting layer containing a light-emitting material between the anode and cathode.

In operation, holes are injected into the device through the anode and electrons are injected through the cathode. Holes in the highest occupied molecular orbital (HOMO) and electrons in the lowest unoccupied molecular orbital (LUMO) of the light-emitting material combine to form an exciton that releases its energy as light.

Cathodes include a single layer of metal such as aluminium, a bilayer of calcium and aluminium as disclosed in WO 98/10621; and a bilayer of a layer of an alkali or alkali earth compound and a layer of aluminium as disclosed in L. S. Hung, C. W. Tang, and M. G. Mason, Appl. Phys. Lett. 70, 152 (1997).

An electron-transporting or electron-injecting layer may be provided between the cathode and the light-emitting layer.

WO 2012/133229 discloses an OLED comprising a charge injection or charge transport layer containing a polymer having a structural unit containing a carboxylate salt substituent.

Bao et al, "Use of a 1H-Benzoimidazole Derivative as an n-Type Dopant and To Enable Air-Stable Solution-Processed n-Channel Organic Thin-Film Transistors" J. Am. Chem. Soc. 2010, 132, 8852-8853 discloses doping of [6,6]-phenyl $C_{61}$ butyric acid methyl ester (PCBM) by mixing (4-(1,3-dimethyl-2,3-dihydro-1H-benzoimidazol-2-yl)phenyl)dimethylamine (N-DMBI) with PCBM and activating the N-DMBI by heating.

US 2014/070178 discloses an OLED having a cathode disposed on a substrate and an electron-transporting layer formed by thermal treatment of an electron-transporting material and N-DMBI. It is disclosed that a radical formed on thermal treatment of N-DMBI may be a n-dopant.

U.S. Pat. No. 8,920,944 discloses n-dopant precursors for doping organic semiconductive materials.

Naab et al, "Mechanistic Study on the Solution-Phase n-Doping of 1,3-Dimethyl-2-aryl-2,3-dihydro-1H-benzoimidazole Derivatives", J. Am. Chem. Soc. 2013, 135, 15018-15025 discloses that n-doping may occur by a hydride transfer pathway or an electron transfer pathway.

It is an object of the invention to provide an organic electronic device comprising a solution-processed, n-doped layer.

SUMMARY OF THE INVENTION

In a first aspect the invention provides a charge-transfer salt formed from a material comprising a repeat unit of formula (I) and an n-dopant:

(I)

wherein BG is a backbone group of the repeat unit; $R^1$ is a ionic substituent comprising at least one cationic or anionic group; n is at least 1; $R^2$ is a non-ionic substituent; and m is 0 or a positive integer; the material further comprising a counterion balancing the charge of the cationic or anionic group.

In a second aspect the invention provides a method of forming a charge-transfer salt according to the first aspect, the method comprising the step of activating a composition comprising the material comprising a repeat unit of formula (I) and the n-dopant to cause the n-dopant to dope the material comprising a unit of formula (I).

In a third aspect the invention provides an organic electronic device comprising a layer comprising a charge-transfer salt according to the first aspect.

In a fourth aspect the invention provides an organic electronic device according to the third aspect wherein the organic electronic device is an organic light-emitting device comprising an anode, a cathode and a light-emitting layer between the anode and the cathode and wherein the layer comprising the charge-transfer salt is an electron injection layer between the light-emitting layer and the cathode.

In a fifth aspect the invention provides a method of forming a device according to the fourth aspect, the method comprising the step of depositing a material comprising a repeat unit of formula (I) from a polar solvent.

In a sixth aspect the invention provides a composition comprising a material comprising a repeat unit of formula (I) and an n-dopant:

(I)

wherein BG is a backbone group of the repeat unit; $R^1$ is a ionic substituent comprising at least one cationic or anionic group; n is at least 1; $R^2$ is a non-ionic substituent; and m is 0 or a positive integer; the material further comprising a counterion balancing the charge of the cationic or anionic group.

In a seventh aspect the invention provides a formulation comprising a composition according to the fifth aspect at least one polar solvent.

In an eighth aspect the invention provides a method of forming a layer of an organic electronic device comprising a charge-transfer salt according to the first aspect, the method comprising the step of depositing a formulation according to the fifth aspect onto a surface; evaporating the at least one solvent; and activating the n-dopant.

DESCRIPTION OF THE DRAWINGS

The invention will now be described in more detail with reference to the drawings in which.

DETAILED DESCRIPTION OF THE INVENTION

Figure 1:
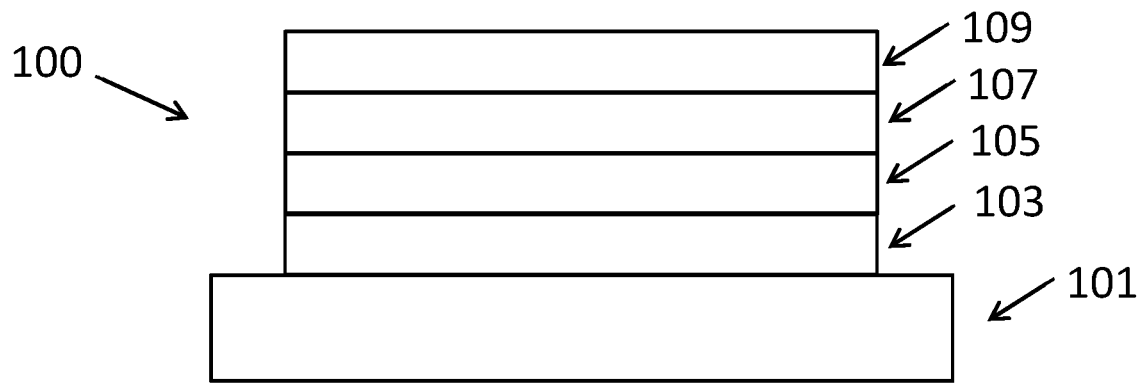
FIG. 1 illustrates schematically an OLED according to an embodiment of the invention.

FIG. 1, which is not drawn to any scale, illustrates an OLED 100 according to an embodiment of the invention supported on a substrate 101, for example a glass or plastic substrate. The OLED 100 comprises an anode 103, a light-emitting layer 105, an electron-injecting layer 107 and a cathode 109.

The anode 103 may be single layer of conductive material or may be formed from two or more conductive layers. Anode 103 may be a transparent anode, for example a layer of indium-tin oxide. A transparent anode 103 and a transparent substrate 101 may be used such that light is emitted through the substrate. The anode may be opaque, in which case the substrate 101 may be opaque or transparent, and light may be emitted through a transparent cathode 109.

Light-emitting layer 105 contains at least one light-emitting material. Light-emitting material 105 may consist of a single light-emitting material or may be a mixture of more than one material, optionally a host doped with one or more light-emitting dopants. Light-emitting layer 105 may contain at least one light-emitting material that emits phosphorescent light when the device is in operation, or at least one light-emitting material that emits fluorescent light when the device is in operation. Light-emitting layer 105 may contain at least one phosphorescent light-emitting material and at least one fluorescent light-emitting material.

Electron-injecting layer 107 comprises or consists of a charge-transfer complex formed from an acceptor material comprising a repeat unit of formula (I) doped by an n-dopant. The charge transfer complex may be formed from a mixture of the acceptor material and a separate n-dopant mixed with the acceptor material, or the n-dopant may be covalently bound to the acceptor material, in which case the material may be a polymer comprising a repeat unit of formula (I) and a co-repeat unit substituted with the n-dopant. In addition to the charge-transfer complex, electron-injection layer 107 may comprise undoped material comprising a unit of formula (I) and/or n-dopant that has not doped the material.

The material comprising a repeat unit of formula (I) may be a non-polymeric or a polymeric material. Preferably, the material is polymeric.

Non-polymeric materials have a polydispersity of 1 and include, without limitation, oligomeric materials comprising 2-10 units of formula (I).

Units of formula (I) in a non-polymeric or oligomeric material may be adjacent one another or may be spaced apart by one or more further units of the material.

Cathode 109 is formed of at least one layer, optionally two or more layers, for injection of electrons into the device.

Preferably, the electron-injecting layer 107 is adjacent to organic light-emitting layer 105.

Preferably, the material comprising a repeat unit of formula (I) has a LUMO that is no more than about 1 eV, optionally less than 0.5 eV or 0.2 eV, deeper (i.e. further from vacuum) than a LUMO of a material of the light-emitting layer, which may be a LUMO of a light-emitting material or a LUMO of a host material if the light-emitting layer comprises a mixture of a host material and a light-emitting material. Optionally, the doped material has a work function that is about the same as a LUMO of a material of the light-emitting layer. Optionally, the material comprising a repeat unit of formula (I) has a LUMO of less (i.e. closer to vacuum) than 3.2 or 3.0 eV from vacuum level, optionally around 2.1 to 2.8 eV from vacuum level.

HOMO and LUMO levels as described herein are as measured by square wave voltammetry.

Preferably, the cathode 109 is in contact with the electron-injecting layer 107.

The OLED 100 may be a display, optionally a full-colour display wherein the light-emitting layer 105 comprises pixels comprising red, green and blue subpixels.

The OLED 100 may be a white-emitting OLED. White-emitting OLEDs as described herein may have a CIE x coordinate equivalent to that emitted by a black body at a temperature in the range of 2500-9000K and a CIE y coordinate within 0.05 or 0.025 of the CIE y co-ordinate of said light emitted by a black body, optionally a CIE x coordinate equivalent to that emitted by a black body at a temperature in the range of 2700-6000K. A white-emitting OLED may contain a plurality of light-emitting materials, preferably red, green and blue light-emitting materials, more preferably red, green and blue phosphorescent light-emitting materials, that combine to produce white light. The light-emitting materials may all be provided in light-emitting layer 105, or one or more additional light-emitting layers may be provided.

A red light-emitting material may have a photoluminescence spectrum with a peak in the range of about more than 550 up to about 700 nm, optionally in the range of about more than 560 nm or more than 580 nm up to about 630 nm or 650 nm.

A green light-emitting material may have a photoluminescence spectrum with a peak in the range of about more than 490 nm up to about 560 nm, optionally from about 500 nm, 510 nm or 520 nm up to about 560 nm.

A blue light-emitting material may have a photoluminescence spectrum with a peak in the range of up to about 490 nm, optionally about 450-490 nm.

Photoluminescence spectra described herein are as measured by casting 5 wt % of the material in a polystyrene film onto a quartz substrate and measuring in a nitrogen environment using apparatus C9920-02 supplied by Hamamatsu.

The OLED 100 may contain one or more further layers between the anode 103 and the cathode 109, for example one or more charge-transporting, charge-blocking or charge-injecting layers. Preferably, the device comprises a hole-injection layer comprising a conducting material between the anode and the light emitting layer 105. Preferably, the device comprises a hole-transporting layer comprising a semiconducting hole-transporting material between the anode 103 and the light emitting layer 105.

The n-dopant may spontaneously dope the material comprising a repeat unit of formula (I) to form the charge-transfer salt, or n-doping may occur upon activation, for example heat or irradiation of the n-dopant and acceptor. If n-doping occurs upon activation then the activation may occur before or after formation of the cathode.

The electron-injecting layer may comprise or consist of the charge-transfer salt.

In forming the electron-injecting layer, the material comprising a repeat unit of formula (I) and n-dopant may be deposited in air.

In forming the electron-injecting layer, the material comprising a repeat unit of formula (I) and the n-dopant (which may covalently bound to the material or may be a separate material mixed with the material) may be deposited from a solution in a solvent, preferably a polar solvent. The solvent or solvent mixture may be selected to prevent dissolution of the underlying layer. Optionally, the or each component of the underlying layer is soluble in, and is deposited from, a non-polar solvent solution.

The n-dopant may also be substituted with ionic substituents, optionally substituents of formula (II) as described below, to enhance its solubility in polar solvents.

The ionic substituent or substituents of the material comprising repeat units of formula (I) may provide enhanced solubility of the material in polar solvents as compared to a material without such ionic substituents.

Preferably, the electron-injecting layer is formed from a solution in a polar solvent. Preferably, the electron-injecting layer is formed on a layer (preferably a light-emitting layer) formed from a solution in a non-polar solvent.

"Solvent" as used herein includes a single solvent or a mixture of two or more solvents. A non-polar solvent may consist of a single non-polar solvent or a plurality of non-polar solvents. A polar solvent may consist of a single polar solvent or a plurality of polar solvents.

Non polar solvents are preferably aprotic. Exemplary non-polar solvents are chloroform, benzenes substituted with one or more substituents selected from $C_{1-10}$ alkyl and $C_{1-10}$ alkoxy groups, for example toluene, xylenes and methylanisoles, and mixtures thereof. Non polar aprotic solvents are preferably aprotic solvents having a dielectric constant at 20° C. of less than 8.

Polar solvents may be protic or aprotic. Exemplary protic solvents are water and alcohols, for example methanol, ethanol, propanol, butoxyethanol, ethylene glycol, 1-methoxy-2-propanol and monofluoro-, polyfluoro- or perfluoro-alcohols, optionally 2,2,3,3,4,4,5,5-octafluoro-1-pentanol. Exemplary aprotic polar solvents are dimethylsulfoxide; propylene carbonate; and 2-butanone. Aprotic polar solvents preferably have a dielectric constant at 20° C. of at least 15 or at least 20.

The backbone of a polymer comprising a unit of formula (I) may be non-conjugated or conjugated. The polymer is preferably a conjugated polymer comprising repeat units of formula (I) conjugated to one another and/or conjugated to aromatic or heteroaromatic groups of co-repeat units adjacent to the repeat units of formula (I).

BG is preferably $Ar^1$; where present $Ar^1$ of formula (I) is preferably a $C_{6-20}$ arylene group, more preferably fluorene.

Preferably, the repeat unit of formula (I) is selected from formulae (Ia) and (Ib):

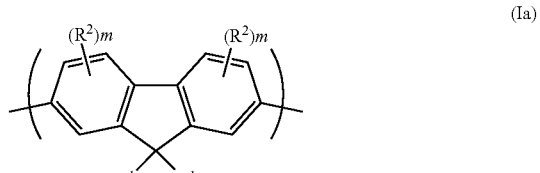

(Ia)

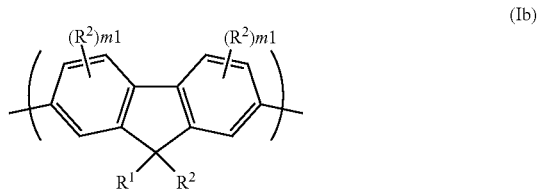

(Ib)

wherein m1 independently in each occurrence is 0 or a positive integer.

m of formula (Ia) is preferably 0.

m1 of formula (Ib) is preferably 0.

$R^1$ is an ionic substituent. "Ionic substituent" as used herein means a substituent that consists of a cationic or anionic group or a substituent that comprises one or more cationic or anionic groups.

Exemplary anionic or cationic substituents $R^1$ have formula (II):

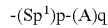

-(Sp$^1$)p-(A)q wherein $Sp^1$ is a spacer group; A is an anion or cation; p is 0 or 1; q is 1 if p is 0; and q is at least 1, preferably 1, if p is 1.

Optionally, $Sp^1$ is selected from:

$C_{1-20}$ alkylene or phenylene-$C_{1-20}$ alkylene wherein one or more non-adjacent C atoms may be replace with O, S or C=O;

a $C_{6-20}$ arylene or 5-20 membered heteroarylene, more preferably phenylene, which may be unsubstituted or substituted with one or more $C_{1-20}$ alkyl groups wherein one or more non-adjacent, non-terminal C atoms of the $C_{1-20}$ alkyl groups may be replaced with O, S, C=O or COO; and a $C_{6-20}$ arylene alkylene spacer group or an alkylene-$C_{6-20}$ arylene spacer group wherein $C_{1-20}$ alkylene and $C_{6-20}$ arylene are as described above and wherein C atoms of alkylene groups may be replaced with O, S or C=O.

"Alkylene" as used herein means a branched or linear divalent alkyl chain.

"non-terminal C atom" of an alkyl group as used herein means a C atom other than the methyl group at the end of an n-alkyl group or the methyl groups at the ends of a branched alkyl chain.

Preferably, $Sp^1$ is selected from:

$C_{1-20}$ alkylene wherein one or more non-adjacent C atoms may be replaced with O, S or CO; and a $C_{6-20}$ arylene or a 5-20 membered heteroarylene, more preferably phenylene, which may be unsubstituted or substituted with one or more substituents. Substituents, if present, are preferably selected from ether groups, optionally polyether groups, preferably a group of formula —O(CH$_2$CH$_2$O)$_v$—R$^{12}$ wherein v is at least 1, optionally an integer from 1 to 10, and $R^{12}$ is a $C_{1-5}$ alkyl group, preferably methyl.

Exemplary anions A may be selected from, without limitation, sulfonate and —COO$^-$. A preferred anion A is —COO$^-$.

Exemplary cations A may be selected from organic or inorganic cations including, without limitation, ammonium; phosphonium; sulfonium; or a heteroaromatic cation, optionally a heteroaromatic cation comprising or consisting of C and N atoms optionally pyridinium, imidzaolium A preferred cation A is —NR$^{16}_3{}^+$ wherein $R^{16}$ in each occurrence is H or $C_{1-12}$ hydrocarbyl. Preferably, each $R^{16}$ is a $C_{1-12}$ hydrocarbyl.

The material comprising repeat units of formula (I) comprises counterions B to balance the charge of the anions or cations A.

A of formula (II) and B may have the same valency, with a counterion B balancing the charge of each A of formula (II).

Anion or cation A may be monovalent or polyvalent. Preferably, A and B are each monovalent.

In another embodiment, the material comprising repeat units of formula (I) may comprise a plurality of anions or cations A wherein the charge of two or more anions or cations A is balanced by a single counterion B. Optionally, the material comprising repeat units of formula (I) comprises di- or trivalent cations B.

Cation B is optionally a metal cation, optionally Li$^+$, Na$^+$, K$^+$, Cs$^+$, preferably Cs$^+$, or an organic cation, optionally ammonium, such as tetraalkylammonium, ethylmethyl imidazolium or pyridinium.

Anion B is optionally halide, optionally F—, Cl—, Br— or I—; an imide, optionally TFSI; a sulfonate group, optionally mesylate or tosylate; hydroxide; carboxylate; sulfate; phosphate optionally PF$_6^-$; phosphinate; phosphonate; or borate, optionally BF$_4^-$.

The one or more ionic substituents $R^1$ may be the only substituents of Ar$^1$ or Ar$^1$ may be substituted with one or more substituents $R^2$ wherein each $R^2$ is independently a non-ionic substituent.

In the case where m is a positive integer, optionally 1, 2, 3 or 4, the group $R^2$ may be selected from:

alkyl, optionally $C_{1-20}$ alkyl, wherein one or more non-adjacent, non-terminal C atoms may be replaced with O, S, C=O or —COO and one or more H atoms may be replaced with F; and a group of formula —(Ar$^2$)$_r$ wherein Ar$^2$ in each occurrence is independently a $C_{6-20}$ aryl or 5-20 membered heteroaryl group that is unsubstituted or substituted with one or more substituents and r is at least 1, optionally 1, 2 or 3.

Preferred non-ionic substituents $R^2$ are ether groups, optionally polyether groups. (Poly)ether groups may have formula —O(CH$_2$CH$_2$O)$_v$—R$^{12}$ wherein v is at least 1, optionally an integer from 1 to 10, and $R^{12}$ is a $C_{1-5}$ alkyl group, preferably methyl.

Ar$^2$ is preferably phenyl. Substituents of Ar$^2$, if present, may independently be selected from substituents $R^{13}$ wherein $R^{13}$ in each occurrence is independently $C_{1-20}$ alkyl wherein one or more non-adjacent, non-terminal C atoms may be replaced with O.

Exemplary repeat units of formula (I) are:

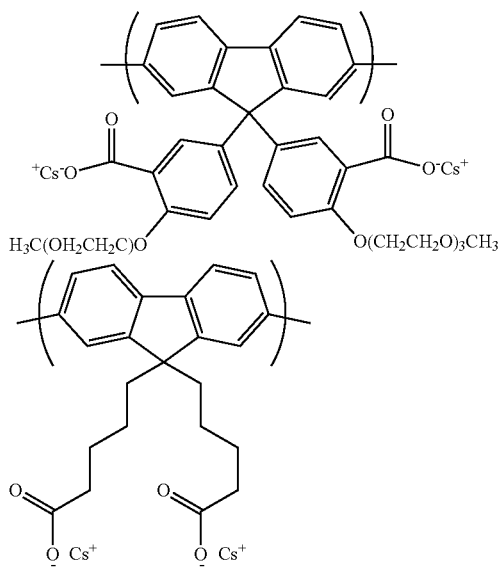

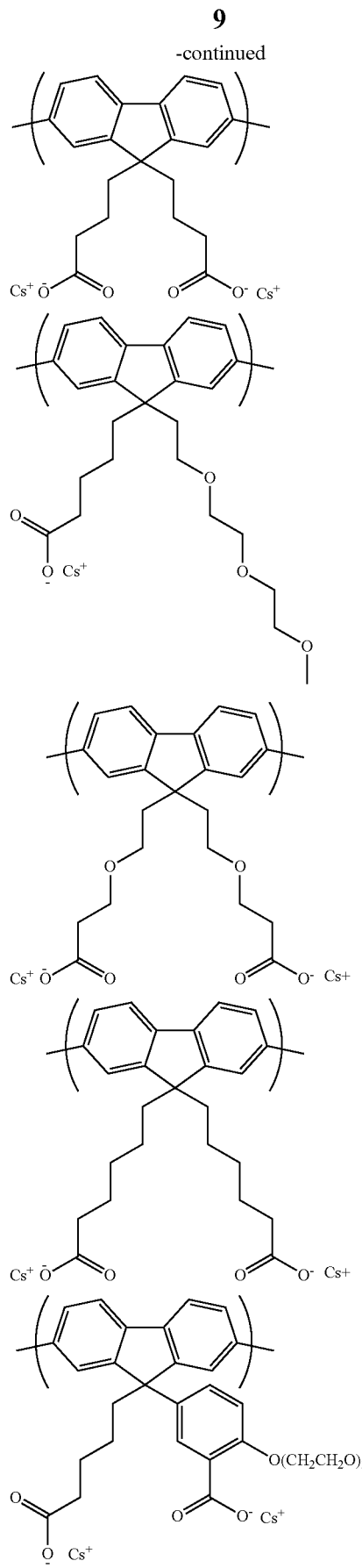
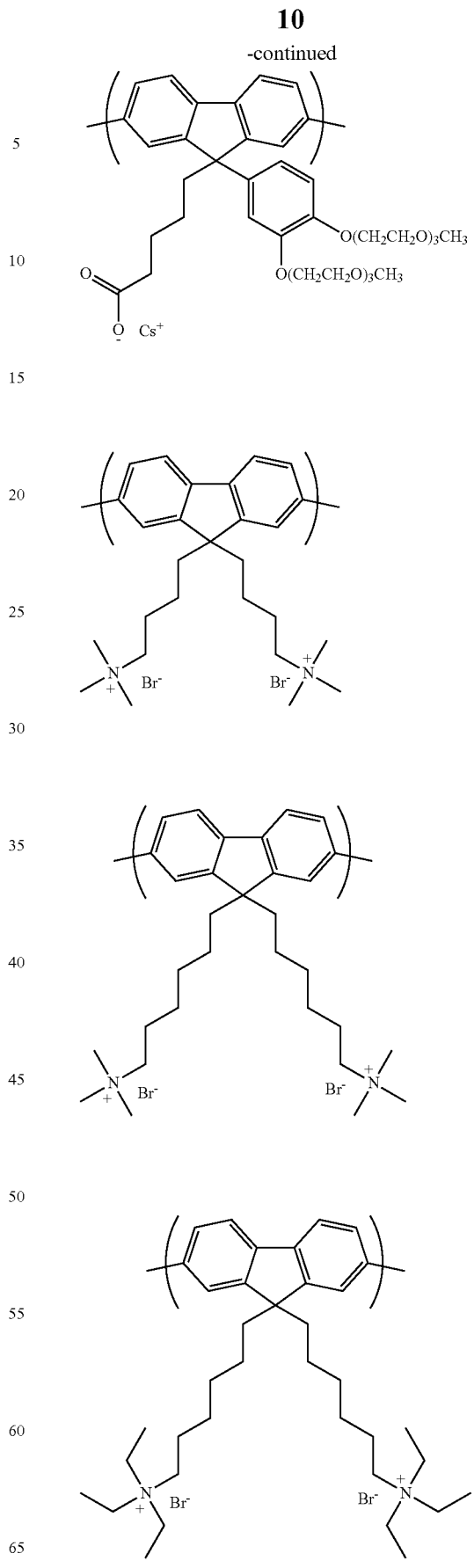

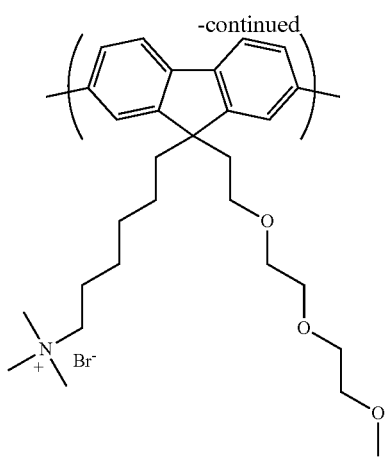

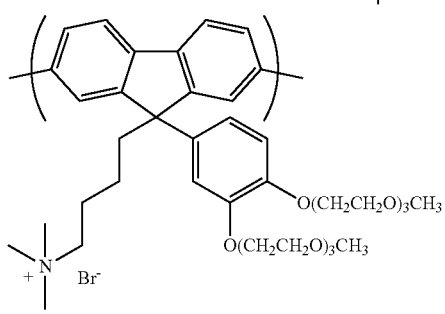

A polymer as described herein may comprise only one repeat unit of formula (I) or may comprise two or more different repeat units of formula (I).

Preferably, the material comprising a repeat unit of formula (I) comprises one or more further units. In the case where the material is a polymer, the further units may form co-repeat units.

Preferably, the polymer is a copolymer comprising repeat units of formula (I) and one or more co-repeat units. If co-repeat units are present then the repeat units of formula (I) may form between 0.1-99 mol % of the repeat units of the polymer, optionally 30-80 or 50-80 mol %.

Exemplary further units, preferably polymeric co-repeat units are $C_{6-20}$ arylene units or 5-20 membered heteroarylene units, each of which may be unsubstituted or substituted with one or more substituents.

Preferred further units include, without limitation, units comprising a polar double or triple bond, optionally a bond selected from a C=N (imino) group, a cyano group, a C=S group, an oxime group or a C=O group, optionally a keto, ester or carbonate group.

Preferably, these polar double- or triple-bond groups are provided as substituents of, and are conjugated to, a $C_{6-20}$ arylene unit, or form part of a conjugated repeat unit, for example fluorenone or benzothiadiazole units.

Benzothiadiazole units may have formula:

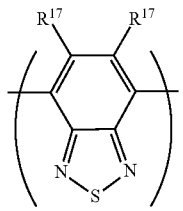

wherein $R^{17}$ in each occurrence is a substituent, optionally a substituent selected from:

alkyl, optionally $C_{1-20}$ alkyl, wherein one or more non-adjacent, non-terminal C atoms of the $C_{1-20}$ alkyl may be replaced with optionally substituted aryl or heteroaryl, O, S, C=O or —COO—, and one or more H atoms may be replaced with F; and aryl or heteroaryl, optionally phenyl, which may be unsubstituted or substituted with one or more substituents.

Exemplary substituents of aryl or heteroaryl groups of $R^{17}$ may be selected from $C_{1-12}$ alkyl wherein one or more non-adjacent, non-terminal C atoms of the $C_{1-12}$ alkyl may be replaced with O, S, C=O or —COO—.

A unit comprising benzothiadiazole may have formula:

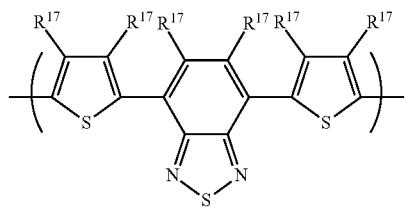

wherein $R^{17}$ is as described above.

A further repeat unit, preferably a polymeric co-repeat unit may have formula (III):

(III)

wherein $Ar^3$ is a $C_{6-20}$ arylene group; $R^4$ is a substituent comprising at least one cyano group; a is at least 1; $R^{17}$ is a substituent as described above; and b is 0 or a positive integer.

$R^4$ may be cyano or it may be a substituent comprising one or more cyano groups.

$R^4$ may be a substituent of formula (IV):

(IV)

wherein $Ar^4$ is a $C_{6-20}$ arylene group; i is at least 1, optionally 1, 2 or 3, $R^6$ is a substituent; and j is 0 or a positive integer, optionally 1, 2, 3 or 4.

$Ar^4$ is preferably phenyl.

In the case where j is a positive integer, $R^6$ may independently in each occurrence be selected from alkyl, optionally $C_{1-20}$ alkyl, wherein one or more non-adjacent, non-terminal C atoms may be replaced with O, S, C=O or —COO and one or more H atoms may be replaced with F.

Repeat units of formula (III) may be selected from formulae (IIIa)-(IIId):

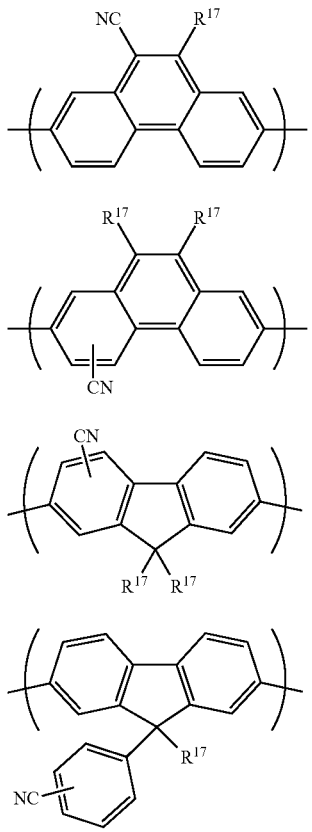

wherein $R^{17}$ is as described above.

Non-polymeric compounds comprising repeat units of formula (I) include compounds of formula (VI):

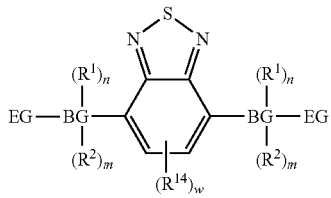

wherein BG, $R^1$, $R^2$, n and m are as described with reference to formula (I); $R^{14}$ is a substituent, optionally a $C_{1-40}$ hydrocarbyl group; w is 0 or a positive integer; and EG is an end group.

EG is optionally H or a $C_{1-40}$ hydrocarbyl group, preferably H.

$C_{1-40}$ hydrocarbyl groups are optionally selected from $C_{1-20}$ alkyl; unsubstituted phenyl; and phenyl substituted with one or more $C_{1-12}$ alkyl groups.

Exemplary compounds of formula (VI) are:

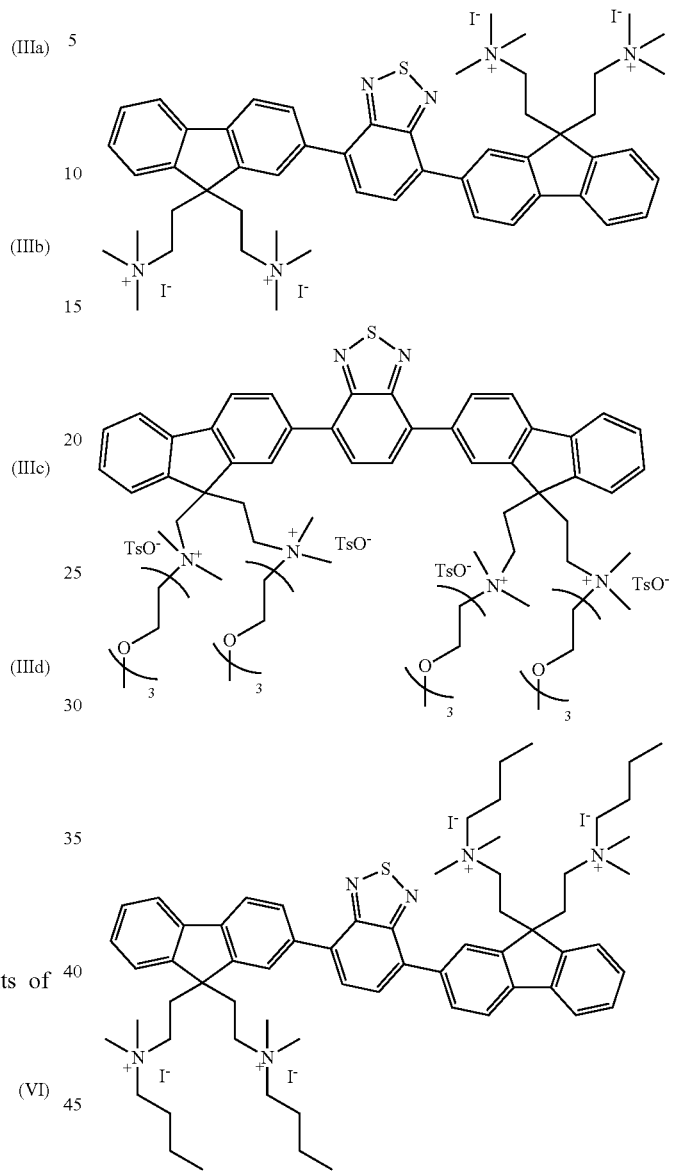

The n-dopant may be mixed with the material comprising a repeat unit of formula (I) or, in the case of a polymeric material, may be bound directly to a co-repeat unit in the polymer backbone, optionally a $C_{6-20}$ arylene co-repeat unit in the polymer backbone, or may be spaced apart therefrom by a spacer group. Exemplary spacer groups are phenylene; $C_{1-20}$ alkylene; and phenylene-$C_{1-20}$ alkylene wherein one or more non-adjacent C atoms of the alkylene group may be replaced with O, S, CO or COO.

Polymers as described anywhere herein suitably have a polystyrene-equivalent number-average molecular weight (Mn) measured by gel permeation chromatography in the range of about $1 \times 10^3$ to $1 \times 10^8$, and preferably $1 \times 10^3$ to $5 \times 10^6$. The polystyrene-equivalent weight-average molecular weight (Mw) of polymers described anywhere herein may be $1 \times 10^3$ to $1 \times 10^8$, and preferably $1 \times 10^4$ to $1 \times 10^7$.

Polymers as described anywhere herein are suitably amorphous polymers.

n-Dopant

In the case where the n-dopant dopes the material comprising a repeat unit of formula (I) spontaneously, it is optionally an n-dopant having a HOMO or semi-occupied molecular orbital (SOMO) level that is shallower (closer to vacuum) than the LUMO level of the acceptor material. Preferably, the n-dopant has a HOMO level that is at least 0.1 eV shallower than the LUMO level of the material comprising a repeat unit of formula (I), optionally at least 0.5 eV. In this case, the n-dopant is preferably an electron donor.

In the case where the n-dopant dopes the material comprising a repeat unit of formula (I) upon activation, the n-dopant has a HOMO level that is the same as or, preferably, deeper (further from vacuum) than the LUMO level of the material comprising a repeat unit of formula (I), optionally at least 1 eV or 1.5 eV deeper. Accordingly, limited or no spontaneous doping occurs upon mixing of the material comprising a repeat unit of formula (I) and such an n-dopant at 20° C., and limited or no spontaneous doping occurs if the n-dopant is covalently bound to the material. An n-dopant may be a hydride donor. An n-dopant may be a material that is capable of converting to a radical that can donate an electron from a SOMO level.

Exemplary n-dopants comprise a 2,3-dihydro-benzoimidazole group, optionally a 2,3-dihydro-1H-benzoimidazole group.

The n-dopant is preferably a group of formula (V):

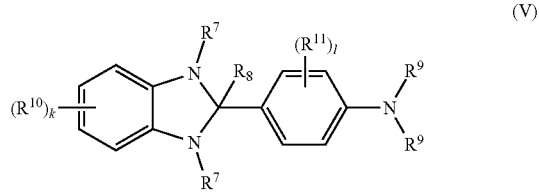

wherein:
each $R^7$ is independently a $C_{1-20}$ hydrocarbyl group, optionally a $C_{1-10}$ alkyl group; $R^8$ is H or a $C_{1-20}$ hydrocarbyl group, optionally H, $C_{1-10}$ alkyl or $C_{1-10}$ alkylphenyl; each $R^9$ is independently a $C_{1-20}$ hydrocarbyl group, optionally $C_{1-10}$ alkyl, phenyl or phenyl substituted with one or more $C_{1-10}$ alkyl groups;
each $R^{10}$ is independently a substituent and k is 0 or a positive integer; and
each $R^{11}$ is independently a substituent and l is 0 or a positive integer.

Preferably, at least one of k and l is at least 1 and $R^{10}$ and/or $R^{11}$ is an ionic substituent, optionally an ionic substituent of formula (II).

Exemplary n-dopants of formula (V) include the following:

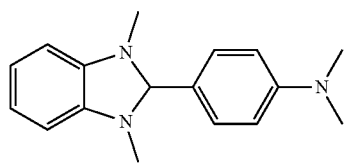

N-DMBI

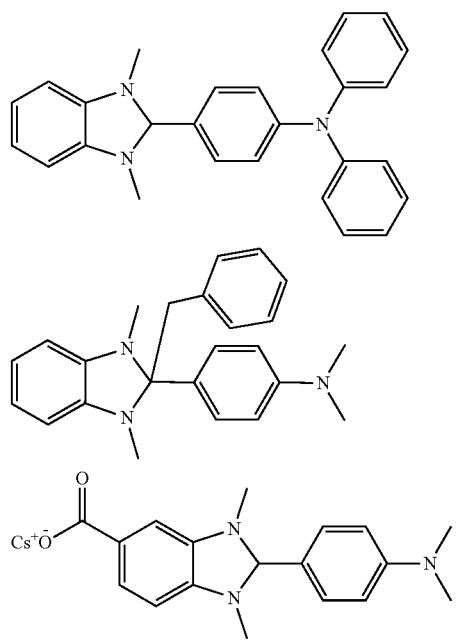

N-DMBI is disclosed in *Adv. Mater* 2014, 26, 4268-4272, the contents of which are incorporated herein by reference.

Other exemplary n-dopants are leuco crystal violet disclosed in J. Phys. Chem. B, 2004, 108 (44), pp 17076-17082, the contents of which are incorporated herein by reference, and NADH.

The n-dopant may be mixed with the material comprising a repeat unit of formula (I) or may be covalently bound thereto.

A substituent $R^{17}$ of a co-repeat unit of a polymer comprising repeat units of formula (I) as described above may comprise or consist of an n-dopant group.

The n-dopant may be bound to a co-repeat unit in the polymer backbone of the polymer comprising a repeat unit of formula (I) or may be spaced apart therefrom by a spacer group. Exemplary spacer groups are phenylene; $C_{1-20}$ alkylene; and phenylene-$C_{1-20}$ alkylene wherein one or more non-adjacent C atoms of the alkylene group may be replaced with O, S, CO or COO.

The n-dopant may be a non-polymeric compound, for example a compound of formula (V), or may be a n-dopant polymer substituted with n-dopant groups that may be covalently bound directly to the backbone of the n-dopant polymer or spaced apart therefrom by a spacer group as described above.

The backbone of an n-dopant polymer may be non-conjugated or may be conjugated. Preferably, the n-dopant polymer is a conjugated polymer comprising unsubstituted or substituted $C_{6-20}$ arylene and/or 5-20 membered heteroarylene repeat units that may be unsubstituted or substituted with one or more substituents $R^1$ and/or $R^2$ as described herein.

n-dopant groups of an n-dopant polymer or n-dopant groups covalently bound to a co-repeat unit of a polymer comprising repeat units of formula (I) include the following:

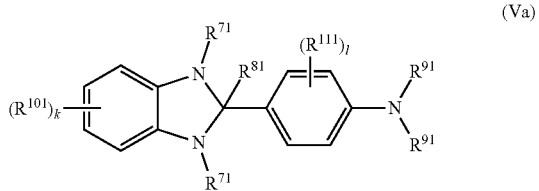

(Va)

wherein $R^{71}$, $R^{81}$, $R^{91}$, $R^{101}$, and $R^{111}$ are as described with reference to $R^7$, $R^8$, $R^9$, $R^{10}$ and $R^{11}$ respectively of formula (V), with the proviso that one of $R^{71}$, $R^{81}$, $R^{91}$, $R^{101}$ and $R^{111}$ is a direct bond to the polymer backbone or to a spacer group between the polymer backbone and the n-doping group of formula (Va); and k and 1 are as described with reference to formula (V). Exemplary spacer groups are phenylene; $C_{1-20}$ alkylene; and $C_{1-20}$ alkylene phenylene, wherein one or more non-adjacent C atoms of the alkylene group may be replaced with O, S, CO or COO. Phenylene groups of the spacer may be unsubstituted or substituted with one or more substituents, optionally substituents selected from $C_{1-12}$ alkyl, $C_{1-12}$ alkoxy and ionic substituents A as described herein.

The backbone of an n-dopant polymer may be non-conjugated or may be conjugated. Preferably, the n-dopant polymer is a conjugated polymer comprising unsubstituted or substituted $C_{6-20}$ arylene and/or or 5-20 membered heteroarylene repeat units in the backbone thereof. Substituents of said arylene or heteroarylene repeat units are optionally selected from ionic substituents $R^1$ and non-ionic substituents $R^2$ as described with reference to formula (I).

The weight ratio of the material comprising a repeat unit of formula (I):n-dopant: may be in the range of 99:1-30:70. Optionally, the n-dopant is present in a molar excess with respect to the material comprising a repeat unit of formula (I).

Polymer Formation

Conjugated polymers comprising repeat units of formula (I) may be formed by polymerising monomers comprising leaving groups that leave upon polymerisation of the monomers to form conjugated repeat units. Exemplary polymerization methods include, without limitation, Yamamoto polymerization as described in, for example, T. Yamamoto, "Electrically Conducting And Thermally Stable pi-Conjugated Poly(arylene)s Prepared by Organometallic Processes", Progress in Polymer Science 1993, 17, 1153-1205, the contents of which are incorporated herein by reference and Suzuki polymerization as described in, for example, WO 00/53656, WO 2003/035796, and U.S. Pat. No. 5,777,070, the contents of which are incorporated herein by reference.

Preferably, the polymer is formed by polymerising monomers comprising boronic acid or boronic ester group leaving groups bound to aromatic carbon atoms of the monomer with monomers comprising leaving groups selected from halogen, sulfonic acid or sulfonic ester, preferably bromine or iodine, bound to aromatic carbon atoms of the monomer in the presence of a palladium (0) or palladium (II) catalyst and a base.

Exemplary boronic esters have formula (XII):

(XII)

wherein $R^6$ in each occurrence is independently a $C_{1-20}$ alkyl group, * represents the point of attachment of the boronic ester to an aromatic ring of the monomer, and the two groups $R^6$ may be linked to form a ring.

The polymer comprising repeat units of formula (I) may be formed by polymerization of a monomer substituted with at least two, preferably only two, leaving groups for forming this repeat unit, optionally with monomers for forming one or more co-repeat units.

The polymer comprising repeat units of formula (I) may be formed by polymerizing monomers for forming a precursor of the polymer comprising non-ionic precursor substituents and converting the non-ionic precursor substituents to ionic substituents to form the polymer comprising repeat units of formula (I). In the case where a repeat unit of formula (I) is substituted with a substituent of formula (II) wherein A is COO—, the non-ionic precursor substituent is preferably an ester group, optionally a group of formula $COOR^{15}$ wherein $R^{15}$ is a hydrocarbyl group, optionally a $C_{1-12}$ alkyl group.

A polymer comprising ester substituents may be converted to a polymer comprising a carboxylate substituent as described in WO 2012/133229, the contents of which are incorporated herein by reference.

The polymer may be end-capped with any suitable end-capping group. An end-capping reactant for forming the end-capping group may be added to the polymerization mixture at the outset of, during or at the end of polymerization. Exemplary end-capping groups are $C_{6-20}$ aryl groups, optionally phenyl.

Non-polymeric materials may be formed by coupling reactions of compounds for forming repeat units of formula (I) substituted with one or two leaving groups, and reacting said compounds with each other or with a compound for forming a further unit of the material comprising repeat units of formula (I).

Activation

In the case where the n-dopant does not spontaneously dope the polymer comprising a repeat unit of formula (I) on contact at 20° C., n-doping may be effected by activation. Preferably, n-doping is effected after formation of a device comprising the layer containing polymer comprising a repeat unit of formula (I) and n-dopant, and optionally after encapsulation. Activation may be by excitation of the n-dopant and/or the polymer comprising a repeat unit of formula (I).

Exemplary activation methods are thermal treatment and irradiation.

Optionally, thermal treatment is at a temperature in the range 80° C. to 170° C., preferably 120° C. to 170° C. or 140° C. to 170° C.

Thermal treatment and irradiation as described herein may be used together.

For irradiation, any wavelength of light may be used, for example a wavelength having a peak in the range of about 200-700 nm.

Optionally, the peak showing strongest absorption in the absorption spectrum of the polymer comprising a repeat unit of formula (I) is in the range of 400-700 nm. Preferably, the strongest absorption of the n-dopant is at a wavelength below 400 nm.

The present inventors have surprisingly found that exposure to electromagnetic radiation of a composition of a polymer comprising a repeat unit of formula (I) and a n-dopant that does not spontaneously dope the polymer comprising a repeat unit of formula (I) results in n-doping even if the electromagnetic radiation is not at the peak absorption wavelength of the n-dopant.

The light emitted from the light source suitably overlaps with an absorption feature, for example an absorption peak or shoulder, of the absorption spectrum of the polymer comprising a repeat unit of formula (I). Optionally, the light emitted from the light source has a peak wavelength within 25 nm, 10 nm or 5 nm of an absorption maximum wavelength of the polymer comprising a repeat unit of formula (I), however it will be appreciated that a peak wavelength of the light need not coincide with an absorption maximum wavelength of the polymer. Optionally, irradiation time is between 1 second and 1 hour, optionally between 1-30 minutes.

In one embodiment, the light emitted from the light source used for irradiation is in the range 400-700 nm. Optionally, the electromagnetic radiation has a peak wavelength greater than 400 nm, optionally greater than 420 nm, optionally greater than 450 nm Optionally, there is no overlap between an absorption peak in the absorption spectrum of the n-dopant and the wavelength(s) of light emitted from the light source.

In another embodiment, the light-emitted from the light source used for irradiation has a peak wavelength of 400 nm or less.

Optionally, the electromagnetic radiation source is an array of inorganic LEDs. The electromagnetic radiation source may produce radiation having one or more than one peak wavelengths.

Preferably, the electromagnetic radiation source has a light output of at least 2000 mW, optionally at least 3000 mW, optionally at least 4000 mW.

Any suitable electromagnetic radiation source may be used to irradiate the film including, without limitation, fluorescent tube, incandescent bulb and organic or inorganic LEDs.

The extent of doping may be controlled by one or more of: the acceptor material/n-dopant ratio; the temperature and duration of heating if activation comprises heating; and the peak wavelength and intensity of the light and the duration of irradiation of the film if activation comprises irradiation.

The n-doped material may be an extrinsic or degenerate semiconductor.

In manufacture of an organic electronic device, such as an OLED as described in FIG. 1, activation may take place during device formation or after the device has been formed. Preferably, activation to cause n-doping takes place after the device has been formed and encapsulated. The device may be manufactured in an environment in which limited or no spontaneous doping occurs, for example a room temperature environment wherein the device is exposed to little or no wavelengths of light that induce n-doping until after encapsulation of the device, for example an environment illuminated by light having a longer wavelength than that of the electromagnetic radiation source such as a clean room illuminated with yellow light.

In the case of an OLED as described in FIG. 1, the material comprising a unit of formula (I) and the n-dopant may be provided between the organic light-emitting layer 105 and the cathode 10.

For activation by irradiation, the film may then irradiated through the anode 101, in the case of a device formed on a transparent substrate 101 and having a transparent anode 103, such as ITO, or the film may be irradiated through the cathode 109 in the case of a device with a transparent cathode. The wavelength used to induce n-doping may be selected to avoid wavelengths that are absorbed by layers of the device between the electromagnetic radiation source and the film.

Light-Emitting Layers

The OLED 100 may contain one or more light-emitting layers.

Light-emitting materials of the OLED 100 may be fluorescent materials, phosphorescent materials or a mixture of fluorescent and phosphorescent materials. Light-emitting materials may be selected from polymeric and non-polymeric light-emitting materials. Exemplary light-emitting polymers are conjugated polymers, for example polyphenylenes and polyfluorenes examples of which are described in Bernius, M. T., Inbasekaran, M., O'Brien, J. and Wu, W., Progress with Light-Emitting Polymers. Adv. Mater., 12 1737-1750, 2000, the contents of which are incorporated herein by reference. Light-emitting layer 107 may comprise a host material and a fluorescent or phosphorescent light-emitting dopant. Exemplary phosphorescent dopants are row 2 or row 3 transition metal complexes, for example complexes of ruthenium, rhodium, palladium, rhenium, osmium, iridium, platinum or gold.

A light-emitting layer of an OLED may be unpatterned, or may be patterned to form discrete pixels. Each pixel may be further divided into subpixels. The light-emitting layer may contain a single light-emitting material, for example for a monochrome display or other monochrome device, or may contain materials emitting different colours, in particular red, green and blue light-emitting materials for a full-colour display.

A light-emitting layer may contain a mixture of more than one light-emitting material, for example a mixture of light-emitting materials that together provide white light emission. A plurality of light-emitting layers may together produce white light.

A fluorescent light-emitting layer may consist of a light-emitting material alone or may further comprise one or more further materials mixed with the light-emitting material. Exemplary further materials may be selected from hole-transporting materials; electron-transporting materials and triplet-accepting materials, for example a triplet-accepting polymer as described in WO 2013/114118, the contents of which are incorporated herein by reference.

Cathode

The cathode may comprise one or more layers. Preferably, the cathode comprises or consists of a layer in contact with the electron injecting layer that comprises or consists of one or more conductive materials. Exemplary conductive materials are metals, preferably metals having a work function of at least 4 eV, optionally aluminium, copper, silver or gold or iron. Exemplary non-metallic conductive materials include conductive metal oxides, for example indium tin oxide and indium zinc oxide, graphite and graphene. Work functions of metals are as given in the CRC Handbook of Chemistry and Physics, 12-114, 87$^{th}$ Edition, published by CRC Press, edited by David R. Lide. If more than one value is given for a metal then the first listed value applies.

The cathode may be opaque or transparent. Transparent cathodes are particularly advantageous for active matrix devices because emission through a transparent anode in such devices is at least partially blocked by drive circuitry located underneath the emissive pixels.

It will be appreciated that a transparent cathode device need not have a transparent anode (unless a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

Hole-Transporting Layer

A hole transporting layer may be provided between the anode 103 and the light-emitting layer 105.

The hole-transporting layer may be cross-linked, particularly if an overlying layer is deposited from a solution. The crosslinkable group used for this crosslinking may be a crosslinkable group comprising a reactive double bond such and a vinyl or acrylate group, or a benzocyclobutane group. Crosslinking may be performed by thermal treatment, preferably at a temperature of less than about 250° C., optionally in the range of about 100-250° C.

A hole transporting layer may comprise or may consist of a hole-transporting polymer, which may be a homopolymer or copolymer comprising two or more different repeat units. The hole-transporting polymer may be conjugated or non-conjugated. Exemplary conjugated hole-transporting polymers are polymers comprising arylamine repeat units, for example as described in WO 99/54385 or WO 2005/049546 the contents of which are incorporated herein by reference. Conjugated hole-transporting copolymers comprising arylamine repeat units may have one or more co-repeat units selected from arylene repeat units, for example one or more repeat units selected from fluorene, phenylene, phenanthrene naphthalene and anthracene repeat units, each of which may independently be unsubstituted or substituted with one or more substituents, optionally one or more $C_{1-40}$ hydrocarbyl substituents.

If present, a hole transporting layer located between the anode and the light-emitting layer 105 preferably has a HOMO level of less than or equal to 5.5 eV, more preferably around 4.8-5.5 eV or 5.1-5.3 eV as measured by cyclic voltammetry. The HOMO level of the hole transport layer may be selected so as to be within 0.2 eV, optionally within 0.1 eV, of an adjacent layer in order to provide a small barrier to hole transport between these layers.

Preferably a hole-transporting layer, more preferably a crosslinked hole-transporting layer, is adjacent to the light-emitting layer 105.

A hole-transporting layer may consist essentially of a hole-transporting material or may comprise one or more further materials. A light-emitting material, optionally a phosphorescent material, may be provided in the hole-transporting layer.

A phosphorescent material may be covalently bound to a hole-transporting polymer as a repeat unit in the polymer backbone, as an end-group of the polymer, or as a side-chain of the polymer. If the phosphorescent material is provided in a side-chain then it may be directly bound to a repeat unit in the backbone of the polymer or it may be spaced apart from the polymer backbone by a spacer group. Exemplary spacer groups include $C_{1-20}$ alkyl and aryl-$C_{1-20}$ alkyl, for example phenyl-$C_{1-20}$ alkyl. One or more carbon atoms of an alkyl group of a spacer group may be replaced with O, S, C=O or COO.

Emission from a light-emitting hole-transporting layer and emission from light-emitting layer 105 may combine to produce white light.

Hole Injection Layers

A conductive hole injection layer, which may be formed from a conductive organic or inorganic material, may be provided between the anode 103 and the light-emitting layer 105 of an OLED as illustrated in FIG. 1 to assist hole injection from the anode into the layer or layers of semi-conducting polymer. Examples of doped organic hole injection materials include optionally substituted, doped poly (ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. Nos. 5,723,873 and 5,798,170; and optionally substituted polythiophene or poly(thienothiophene). Examples of conductive inorganic materials include transition metal oxides such as VOx MoOx and RuOx as disclosed in Journal of Physics D: Applied Physics (1996), 29(11), 2750-2753.

Encapsulation

In the case where the n-dopant does not spontaneously dope the material comprising a unit of formula (I), the n-dopant is preferably activated to cause n-doping as described herein after encapsulation of the device containing the film to prevent ingress of moisture and oxygen.

Suitable encapsulants include a sheet of glass, films having suitable barrier properties such as silicon dioxide, silicon monoxide, silicon nitride or alternating stacks of polymer and dielectric or an airtight container. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

The substrate on which the device is formed preferably has good barrier properties such that the substrate together with the encapsulant form a barrier against ingress of moisture or oxygen. The substrate is commonly glass, however alternative substrates may be used, in particular where flexibility of the device is desirable. For example, the substrate may comprise one or more plastic layers, for example a substrate of alternating plastic and dielectric barrier layers or a laminate of thin glass and plastic.

Formulation Processing

Light-emitting layer 105 and electron-injecting layer 107 may be formed by any method including evaporation and solution deposition methods. Solution deposition methods are preferred.

Formulations suitable for forming light-emitting layer 105 and electron-injecting layer 107 may each be formed from the components forming those layers and one or more suitable solvents.

Preferably, light-emitting layer 105 is formed by depositing a solution in which the solvent is one or more non-polar solvent materials, optionally benzenes substituted with one or more substituents selected from $C_{1-10}$ alkyl and $C_{1-10}$ alkoxy groups, for example toluene, xylenes and methylanisoles, and mixtures thereof.

Preferably, the electron-injecting layer 107 is formed by depositing a polymer comprising a repeat unit of formula (I) and an n-dopant together, preferably from a solution.

Preferably, the electron-injecting layer is formed from a polar solvent, which may avoid or minimise dissolution of the underlying layer if the materials of the underlying layer are not soluble in polar solvents.

Particularly preferred solution deposition techniques including printing and coating techniques such spin-coating, inkjet printing and lithographic printing.

Coating methods are particularly suitable for devices wherein patterning of the light-emitting layer is unnecessary—for example for lighting applications or simple monochrome segmented displays.

Printing methods are particularly suitable for high information content displays, in particular full colour displays. A device may be inkjet printed by providing a patterned layer over the anode and defining wells for printing of one colour (in the case of a monochrome device) or multiple colours (in the case of a multicolour, in particular full colour device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, slot die coating, roll printing and screen printing.

Applications

A layer comprising the doped polymer comprising repeat units of formula (I) has been described with reference to the electron-injection layer of an organic light-emitting device formed over an organic light-emitting layer, however it will be appreciated that the layer formed as described herein may be used in other organic electronic devices, and may be formed on a surface of said organic electronic device by methods as described herein, for example as an electron-extraction layer of an organic photovoltaic device or organic photodetector; as an auxiliary electrode layer of a n-type organic thin film transistor or as an n-type semiconductor in a thermoelectric generator.

Measurements

UV-visible absorption spectra of pristine and n-doped acceptor materials as described herein were measured by spin-coating onto glass substrates, as blend with the dopant.

The film thicknesses were in the range of 20-100 nm.

After spin-coating and drying, the polymer films were encapsulated in a glove box, in order to exclude any contact of the n-doped films with air.

After the encapsulation, UV-vis absorption measurements were conducted with a Carey-5000 Spectrometer, followed by successive exposures to visible light and repeat UV-VIS measurements.

HOMO, SOMO and LUMO levels as described anywhere herein are as measured by square wave voltammetry.

Equipment:

CHI660D Electrochemical workstation with software (IJ Cambria Scientific Ltd))

CHI 104 3 mm Glassy Carbon Disk Working Electrode (IJ Cambria Scientific Ltd))

Platinum wire auxiliary electrode

Reference Electrode (Ag/AgCl) (Havard Apparatus Ltd)

Chemicals

| | |
|---|---|
| Acetonitrile (Hi-dry anhydrous grade-ROMIL) | (Cell solution solvent) |
| Toluene (Hi-dry anhydrous grade) | (Sample preparation solvent) |
| Ferrocene - FLUKA | (Reference standard) |
| Tetrabutylammoniumhexafluoro-phosphate-FLUKA) | (Cell solution salt) |

Sample Preparation

The acceptor polymers were spun as thin films (~20 nm) onto the working electrode; the dopant material was measured as a dilute solution (0.3 w %) in toluene.

Electrochemical Cell

The measurement cell contains the electrolyte, a glassy carbon working electrode onto which the sample is coated as a thin film, a platinum counter electrode, and a Ag/AgCl reference glass electrode. Ferrocene is added into the cell at the end of the experiment as reference material (LUMO (ferrocene)=−4.8 eV).

Material Synthesis Examples n-Dopant 1 n-dopant 1 was prepared according to the following reaction scheme:

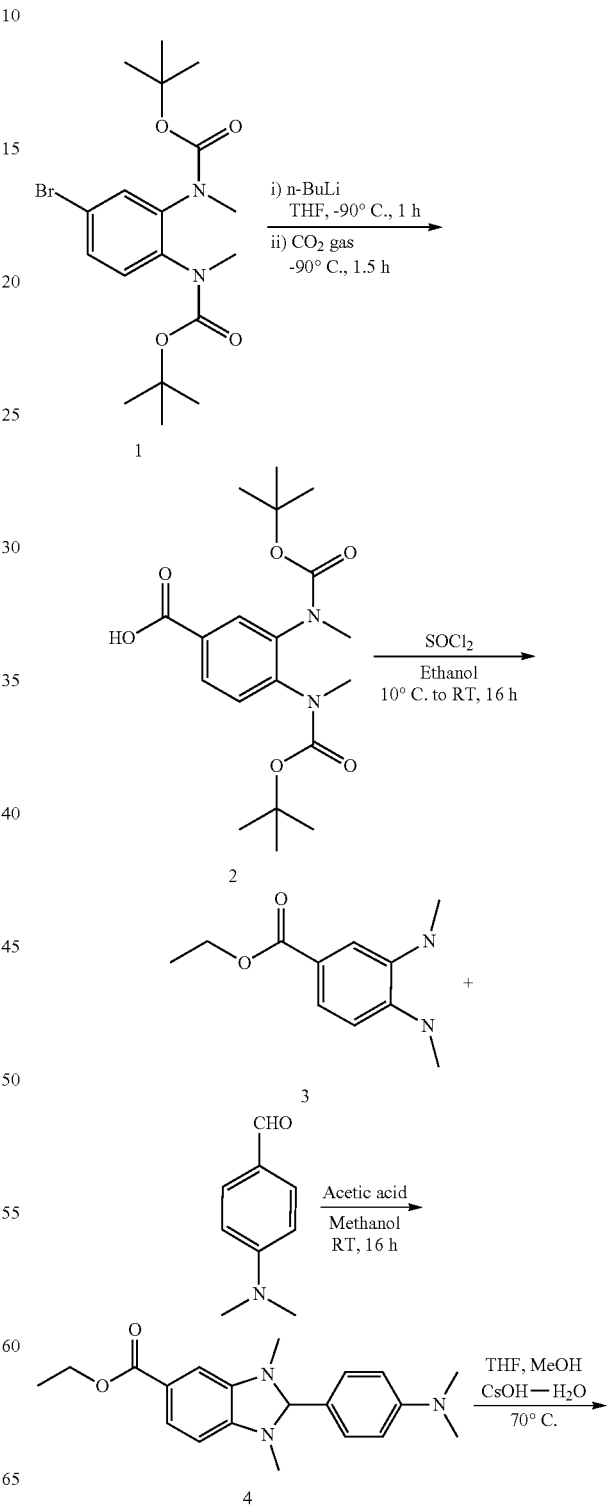

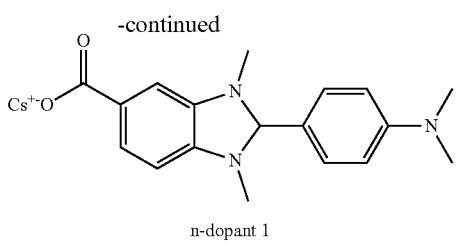

n-dopant 1

Intermediate 2:

A solution of Intermediate 1 (23.6 g, 0.0568 mol) in tetrahydrofuran (120 ml) was cooled to −90° C. N-BuLi (2.5M in n-hexane, 34 ml, 0.0852 mol) was added slowly to the mixture at −90° C. and stirred for 1 hour at −90° C. Carbon dioxide gas was bubbled in the reaction mass for 1.5 hours at −90° C. Reaction mixture was allowed to warm up to room temperature slowly and quenched by adding water (150 ml). Organic layer was separated and aqueous layer was extracted with ethyl acetate (200 ml×2). Combined organic layer was washed with water (300 ml), brine (300 ml), dried over sodium sulfate and concentrated under reduce pressure. The crude material was adsorbed on celite and purified by column chromatography over silica gel using 3% methanol in chloroform as eluent to obtain 18 g of Intermediate 2 with 94.68% HPLC purity as a pale orange color viscous liquid, 65% yield.

$^1$H-NMR (400 MHz, DMSO D$_6$: δ [ppm] 1.36 (s, 18H), 3.32 (s, 6H), 7.39 (d, J=8 Hz, 1H), 7.76 (s, 1H) 7.83 (d, J=2.00 Hz, 1H)

Intermediate 3:

A solution of Intermediate 2 (18 g, 0.0473 mol) in ethanol (180 mL) was cooled to 0° C. and thionyl chloride (28.14 g, 0.236 mol) was added drop wise for 10 minutes. Reaction mixture was then stirred for 16 hours at room temperature. Reaction mixture was poured into ice (200 g), stirred for 30 minutes and basified by adding 10% aqueous sodium bicarbonate solution. The mixture was extracted with ethyl acetate (100 ml×3). Combined organic layers were washed with water (200 ml), brine (300 ml), dried over sodium sulfate and concentrated under reduced pressure. The crude material was adsorbed on celite and purified by column chromatography over silica gel (neutralized with triethyl amine) using 13% ethyl acetate in hexane as eluent to obtain 4.2 g Intermediate 3 with 99.32% HPLC purity as a pale orange color liquid, 42% yield.

$^1$H-NMR (400 MHz, CDCl$_3$): δ [ppm] 1.39 (t, J=7.20 Hz, 3H), 2.90 (s, 6H), 4.35 (q, J=6.80 Hz, 2H), 6.62 (d, J=8.4 Hz, 1H), 7.39 (s, 1H) 7.64 (d, J=2.00 Hz, 1H)

Intermediate 4:

Nitrogen was bubbled for 10 minutes into a solution of 4-N,N-Dimethyl amino benzaldehyde (3 g, 0.0201 mol) in anhydrous methanol (20 ml). Intermediate 3 (4.2 g, 0.0201 mol) was added and nitrogen bubbling continued for another 5 minutes. Glacial acetic acid (1 mL) was added and mixture was stirred at room temperature for 16 hours. The reaction was cooled to 0° C. and filtered. Solid was washed with cold methanol (10 ml) and dried to obtain 1.8 g fraction of Intermediate 4 with 99.01% HPLC purity as a white solid and 1.1 g fraction of Intermediate 4 with 97.51% HPLC purity as a white solid, 43% yield.

$^1$H-NMR (400 MHz, CDCl$_3$): δ [ppm] 1.37 (t, J=7.20 Hz, 3H), 2.57 (d, J=8.4 Hz, 6H), 2.98 (s, 6H), 4.3 (q, J=6.80 Hz, 2H), 5.09 (s, 1H), 6.36 (d, J=8.00 Hz, 1H), 6.82 (dd, J=1.6 Hz J=6.80 Hz, 2H), 6.9 (s, 1H), 7.37 (dd, J=2 Hz J=6.80 Hz, 2H), 7.46 (dd, J=1.6 Hz J=8.8 Hz, 1H) n-dopant 1:

Nitrogen was bubbled in a mixture of Intermediate 4 (5.000 g, 14.73 mmol) and tetrahydrofuran (25 ml) for 5 minutes followed by the addition of methanol (10 ml) and a solution of cesium hydroxide monohydrate (7.421 g, 44.19 mmol) in water (5 ml). Nitrogen was bubbled into the mixture for 10 minutes after which the mixture was heated to 70° C. for 16 hours. Once cooled, the mixture was evaporated to dryness under reduced pressure. The residue was dissolved in water and purified by column chromatography over C18 reversed phase silica, using a gradient of water to water:methanol 1:1 as eluent. The combined fractions containing n-dopant 1 were evaporated to dryness under reduced pressure and the residue was triturated with acetonitrile (100 ml), filtered and dried in a vacuum oven for 16 hours at 50° C. to afford 4.976 g of n-dopant 1 as a white powder at 99% purity by NMR, 76% yield.

$^1$H-NMR (600 MHz, MeOH-D$_4$): δ$_H$ [ppm] 2.51 (s, 3H), 2.53 (s, 3H), 2.95 (s, 6H), 4.77 (s, 1H), 6.34 (d, J=7.8 Hz, 1H), 6.79-6.81 (m, 2H), 7.04 (d, J=1.5 Hz, 2H), 7.36-7.39 (m, 2H), 7.41 (dd, J=7.8 Hz, J=1.6 Hz, 1H).

Acceptor Unit 1

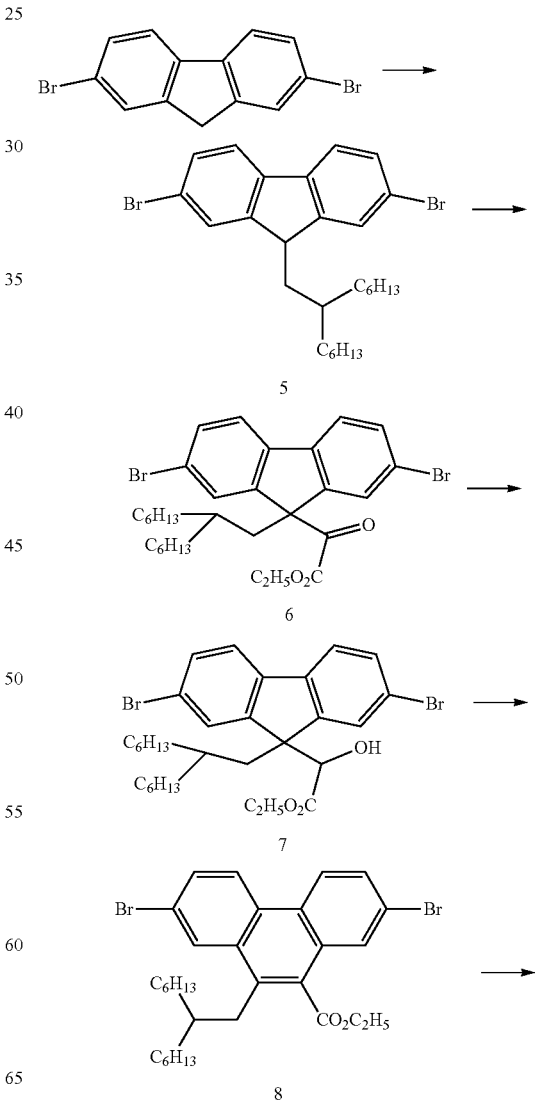

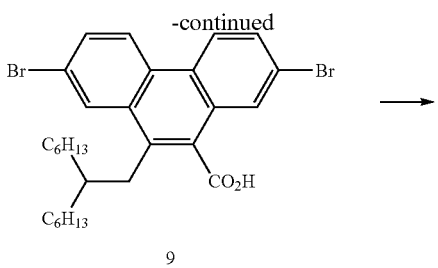

9

10

Acceptor Unit 1

Intermediate 5:

To a mixture of 2,7-dibromofluorene (150 g, 0.4629 mol) in diethyl ether (1.2 L) was added n-BuLi (203.7 ml, 0.5092 mol) at room temperature. The reaction mixture was stirred at room temperature for 2 hours. 1-bromo-2-hexyloctane (146.25 g, 0.5555 mol) in diethyl ether (1.2 L) was added to it slowly at room temperature. The reaction mixture was stirred at room temperature for 16 hours. Citric acid solution (20% aqueous, 1500 ml) was added and mixture was extracted with ethyl acetate (2000 ml×2). The combined organic layer were washed with brine (1000 ml), dried over sodium sulphate and concentrated. Residue was purified twice by column chromatography using silica gel and hexanes as eluent to obtain 153 g of Intermediate 5 as yellow viscous oil, 64% yield.

$^1$H-NMR (400 MHz, CDCl3): δ [ppm] 0.90 (t, J=7.00 Hz, 6H), 1.25-1.38 (m, 20H), 1.62-1.69 (m, 1H), 1.75 (t, J=6.80 Hz, 2H), 3.96 (t, J=6.76 Hz, 1H), 7.49 (dd, J=1.56, 8.10 Hz, 2H), 7.58 (d, J=8.12 Hz, 2H), 7.62 (s, 2H).

Intermediate 6:

To a suspension of sodium hydride (15.38 g, 0.3849 mol) in tetrahydrofuran (500 ml) was added slowly a solution of Intermediate 5 (100 g, 0.1923 mol) in tetrahydrofuran (200 ml) at room temperature. The reaction mixture was stirred at room temperature for 4 hours. It was then added to a solution of ethyl oxalyl chloride (52.5 g, 0.3849 mol) in tetrahydrofuran (300 ml) at −20° C. The reaction mixture temperature was allowed to warm up to room temperature and stirred for 16 hours. It was poured into ice-water and extracted with ethyl acetate (500 ml×2). Combined ethyl acetate layers were dried over sodium sulphate and concentrated. The was purified by column chromatography using silica gel and 2% ethyl acetate in hexanes as eluent to obtain 63 g of Intermediate 6, 53 yield.

Intermediate 7:

To a solution of Intermediate 6 (120 g, 0.1934 mol) in tetrahydrofuran (1200 ml) was added lithium aluminium hydride (25.14 ml, 2M solution in tetrahydrofuran, 0.0503 mol) at −20° C. The reaction mixture was then stirred at room temperature for 5 hours. Ethyl acetate (100 ml) was added to it and mixture was filtered through celite. The filtrate was concentrated and residue was purified by column chromatography using silica gel and a gradient of 2% to 5% ethyl acetate in hexanes as eluent to obtain 91 g of Intermediate 7, 76% yield.

Intermediate 8:

To a solution of Intermediate 7 (90 g, 0.1446 mol) in toluene (900 ml) was added phosphorus pentoxide (82 g, 0.5784 mol) at room temperature. The reaction mixture was heated to 110° C. and stirred for 5 hours. It was then cooled to room temperature and ice-water (1000 ml) was added to it. The mixture was extracted with ethyl acetate (500 ml×2). Combined organic layers were washed with brine (500 ml), dried over sodium sulphate and concentrated. Residue was purified twice by column chromatography using silica gel and 2% ethyl acetate in hexanes as eluent to obtain 49 g of Intermediate 8, 56% yield.

Intermediate 9:

To a solution of Intermediate 8 (49 g, 0.08111 mol) in a mixture of tetrahydrofuran (250 ml) and methanol (250 ml) was added potassium hydroxide powder (90.8 g, 1.6212 mol). The mixture was heated to 130° C. in a sealed tube and stirred for 40 hours. The reaction was cool to −10° C. and concentrated hydrochloric acid (120 ml) was added it until acidic pH was obtained. The mixture was extracted with ethyl acetate (500 ml×2). Combined ethyl acetate layers were dried over sodium sulphate and concentrated. Residue was purified by column chromatography using silica gel and a gradient of 5% to 10% ethyl acetate in hexanes as eluent to obtain 25.3 g of Intermediate 9, 54% yield.

$^1$H-NMR (300 MHz, DMSO-d6): δ [ppm] 0.75 (t, J=6.93 Hz, 6H), 1.08-1.38 (m, 20H), 1.75-1.92 (m, 1H), 3.05 (d, J=6.87 Hz, 2H), 7.83-7.87 (m, 2H), 7.90 (s, 1H), 8.29 (s, 1H), 8.80-8.85 (m, 2H).

Intermediate 10:

A solution of Intermediate 9 (25 g, 0.0434 mol) in thionyl chloride (250 ml) was refluxed for 3 hours. Thionyl chloride was then distilled off and crude acid chloride was dissolved in tetrahydrofuran (200 ml). It was added to the solution of ammonia gas in tetrahydrofuran (800 ml) at −20° C. The mixture was then stirred at room for 3 hours. Tetrahydrofuran was distilled off and the residue was diluted with water. It was extracted with ethyl acetate (500 ml×2). Combined organic layers were dried over sodium sulphate and concentrated. The residue was purified by column chromatography using silica gel and 10% ethyl acetate in hexanes as eluent to obtain 22.4 g of Intermediate 10, 90% yield.

Acceptor Unit 1:

To a solution of Intermediate 10 (22 g, 0.0383 mol) in toluene (440 ml) was added phosphorus pentoxide (10.8 g, 0.0766 mol). Reaction mixture was heated to 110° C. and stirred for 4 hours. The reaction mixture was allowed cool down to room temperature and quenched over ice water (500 ml). The mixture was extracted with ethyl acetate (500 ml×2), dried over sodium sulphate and concentrated. The residue was purified by column chromatography using silica gel and 100% hexane as eluent to obtain 20.6 g of Acceptor Unit 1 as an off-white solid, 99.4% pure by HPLC, 97% yield.

$^1$H-NMR (400 MHz, CDCl3): δ [ppm] 0.87 (t, J=6.92 Hz, 6H), 1.12-1.39 (m, 16H), 1.41-1.50 (m, 4H), 1.87-1.98 (m, 1H), 3.34 (d, J=7.20 Hz, 2H), 7.82 (dd, J=1.96, 8.86 Hz, 1H), 7.89 (dd, J=1.88, 8.88 Hz, 1H), 8.30 (s, 1H), 8.87 (s, 1H), 8.48 (d, J=8.64 Hz, 1H), 8.54 (d, J=8.96 Hz, 1H).

Monomer Precursor 2:

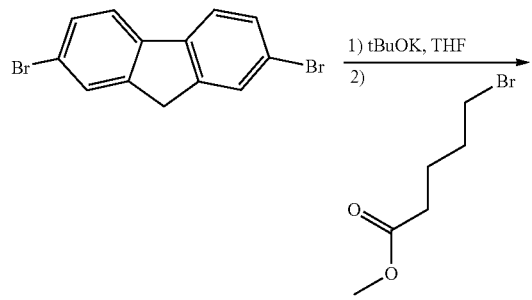

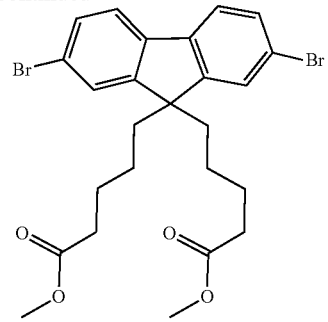

Monomer Precurssor 2

Nitrogen was bubbled into a solution of 2,7-dibromofluorene (20.0 g, 61.7 mmol) in tetrahydrofuran (200 ml) for 1 hour. Potassium tert-butoxide (20.8 g, 185.4 mmol) was added to it at 4° C. Mixture was stirred for 1 hour at room temperature and methyl 5-bromopentanoate (26.9 g, 137.9 mmol) in solution in tetrahydrofuran (200 ml) was added to it dropwise at 10° C. Reaction was stirred overnight at room temperature. It was cooled down to 5° C. and quenched by adding water (200 ml) dropwise. Mixture was extracted with dichlorometane (×2). Combined organic phases were dried over magnesium sulphate, and concentrated under reduced pressure. Residue was filtered through a silica/florisil plug (2.5 cm florisil on top of 6 cm silica), eluted with dichloromethane.

Filtrate was concentrated and resulting solid was recrystallized three times from acetonitrile to yield 13.8 g of Monomer Precursor 2 as a white solid, 98.83% pure by HPLC, 40% yield.

$^1$H-NMR (600 MHz, CDCl3): δ [ppm] 0.58 (m, 4H), 1.39 (quint, 4H), 1.93 (m, 4H), 2.06 (t, 4H), 3.55 (s, 6H), 7.41 (d, J=1.7 Hz, 2H), 7.43 (dd, J=1.7, 8.1 Hz, 2H), 7.50 (d, J=8.2 Hz, 2H).

Polymer Example 1

Polymer Example 1 has the following structure:

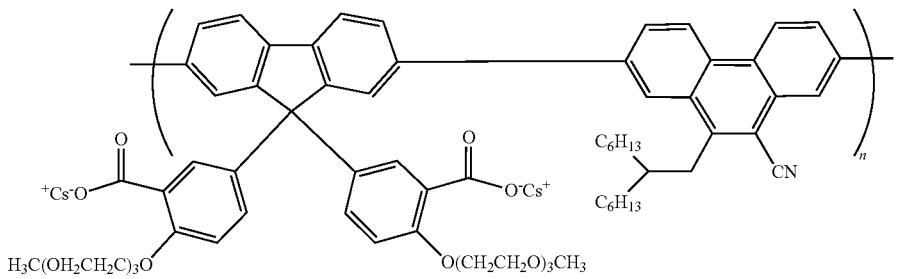

Polymer Example 1 was formed by Suzuki polymerization as disclosed in WO00/53656 of 50 mol % each of the following monomers to form a precursor polymer followed by hydrolysis of the precursor polymer:

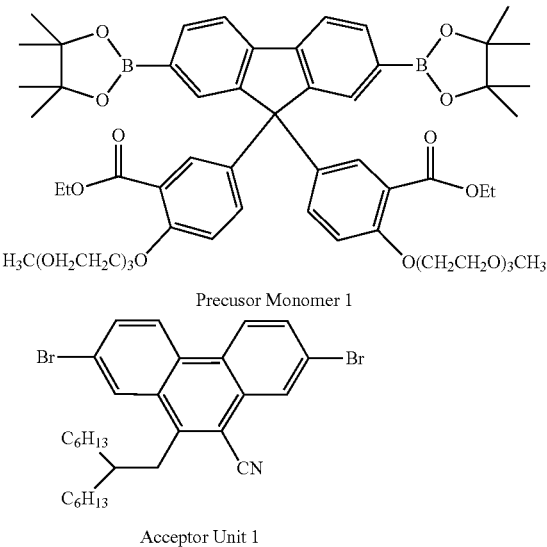

Precursor Monomer 1

Acceptor Unit 1

To hydrolyse the polymer and form its cesium salt, nitrogen was bubbled for 30 minutes in 113 ml of tetrahydrofuran, in 42 ml of methanol and in a solution of cesium hydroxide monohydrate (0.80 g, 4.73 mmol) in 3.4 ml of water. 2.24 g of the precursor polymer was suspended in the tetrahydrofuran and heated up to 65° C. Mixture was stirred until full dissolution of the polymer. Methanol was added drop wise followed by the cesium hydroxide solution. The mixture was stirred at 65° C. for 16 hours and cooled down to room temperature. The solution was filtered and concentrated to 42 ml and it was precipitated into 800 ml of diethyl ether. The slurry was stirred for 10 minutes and filtered. The polymer was dried in vacuum oven at 50° C. overnight to yield 2.52 g of Polymer Example 1, 96% yield.

The precursor polymer had a Mz of 78,000, a Mw of 59,000, an Mp of 68,000, an Mn of 37,000 and a Pd of 1.58.

Polymer Example 1 has a LUMO level of −2.53 eV.

Device Example 1

Green phosphorescent devices having the following structure were prepared:
ITO/HIL (50 nm)/LEL (80 nm)/EIL (20 nm)/Ag (100 nm) in which ITO is an indium tin oxide anode; HIL is a hole-injection layer; EIL is an electron injection layer and LEL is a light-emitting layer.

To form the devices, a substrate carrying ITO was cleaned using UV/Ozone. The hole injection layer was formed by spin-coating an aqueous formulation of a hole-injection material available from Nissan Chemical Industries and heating the resultant layer. The light-emitting layer was formed by spin-coating Host Polymer 1 and Green Phosphorescent Emitter 1 with a light-emitting dopant from xylene solution in a glove box. The electron-injection layer was formed by spin-coating a formulation of Polymer Example 1 and n-dopant 1 from methanol solution in a ratio as given in Table 1. The cathode was formed by evaporation of silver.

After spin-coating the electron injection layer, the EIL was dried at 80° C. for 10 min, in a glovebox, followed by deposition of the cathode by thermal evaporation in vacuum.

The devices were then encapsulated and heated at 80° C. for 10 minutes.

TABLE 1

| Device | Acceptor Polymer 1:Compound Example 1 wt:wt |
|---|---|
| Device Example 1A | 90:10 |
| Device Example 1B | 80:20 |
| Device Example 1C | 60:40 |

Host Polymer 1 is a block copolymer formed by Suzuki polymerization as described in WO 00/53656 of the following monomers:

Block 1:

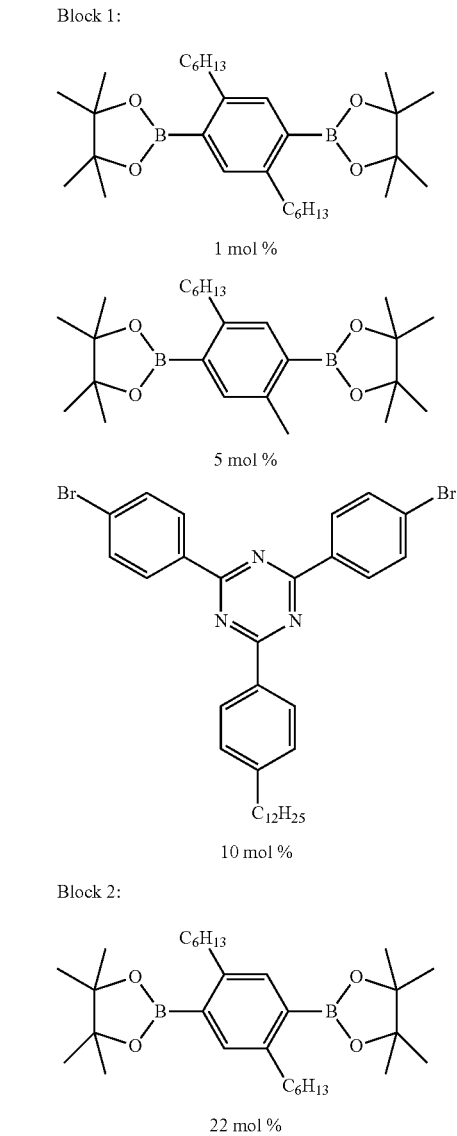

1 mol %

5 mol %

10 mol %

Block 2:

22 mol %

-continued

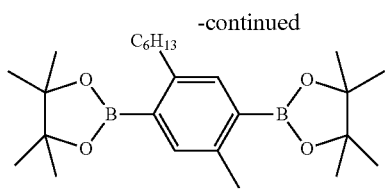

22 mol %

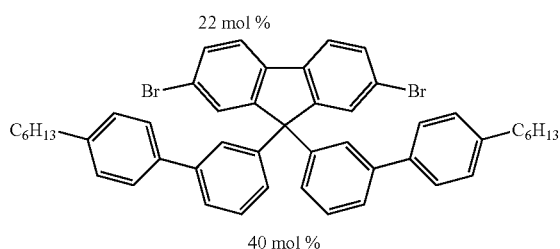

40 mol %

Green Phosphorescent Emitter 1 has the following structure:

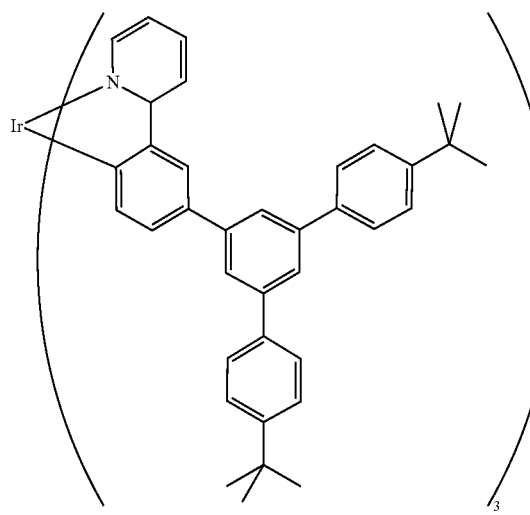

Figure 2:
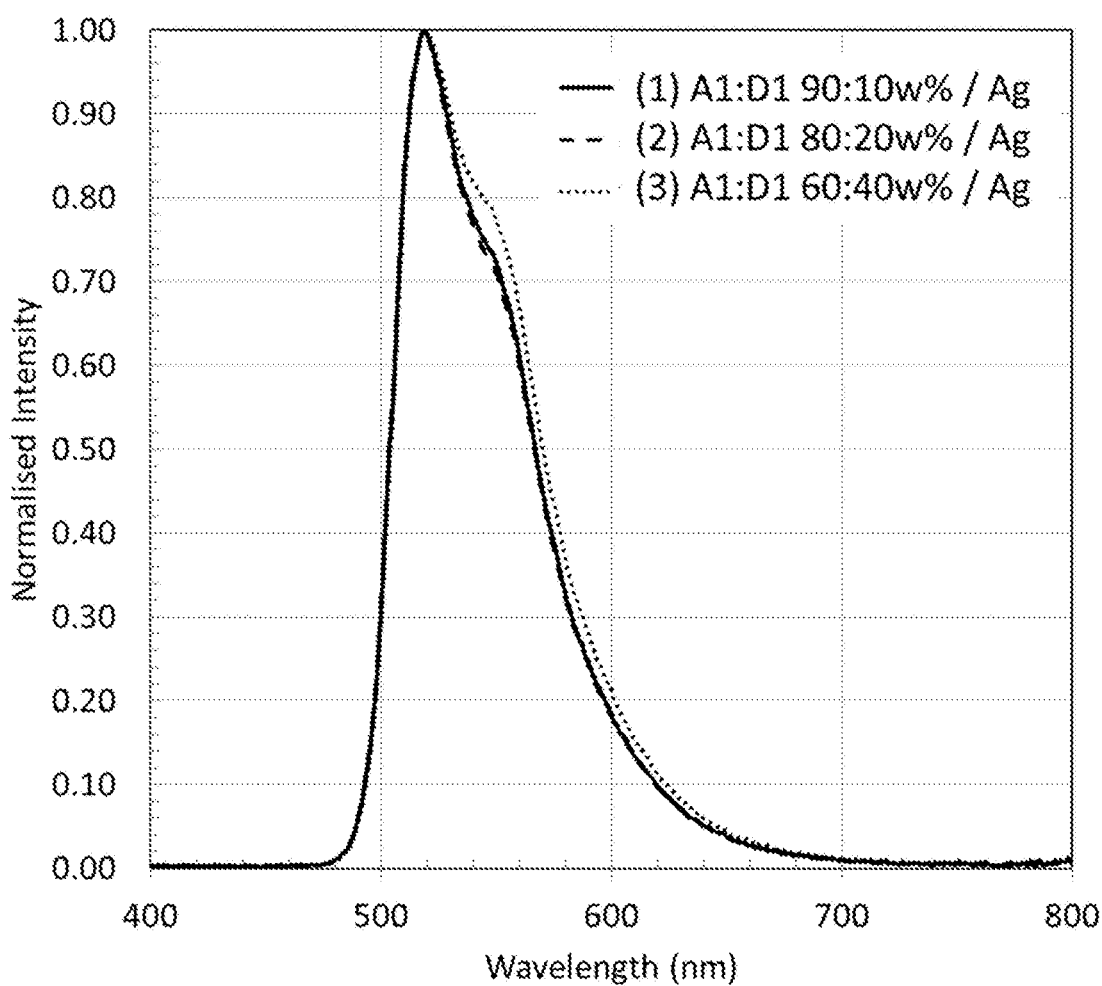
FIG. 2 shows the electroluminescent spectra for green light emitting OLEDs according to embodiments of the invention.
Figure 3:
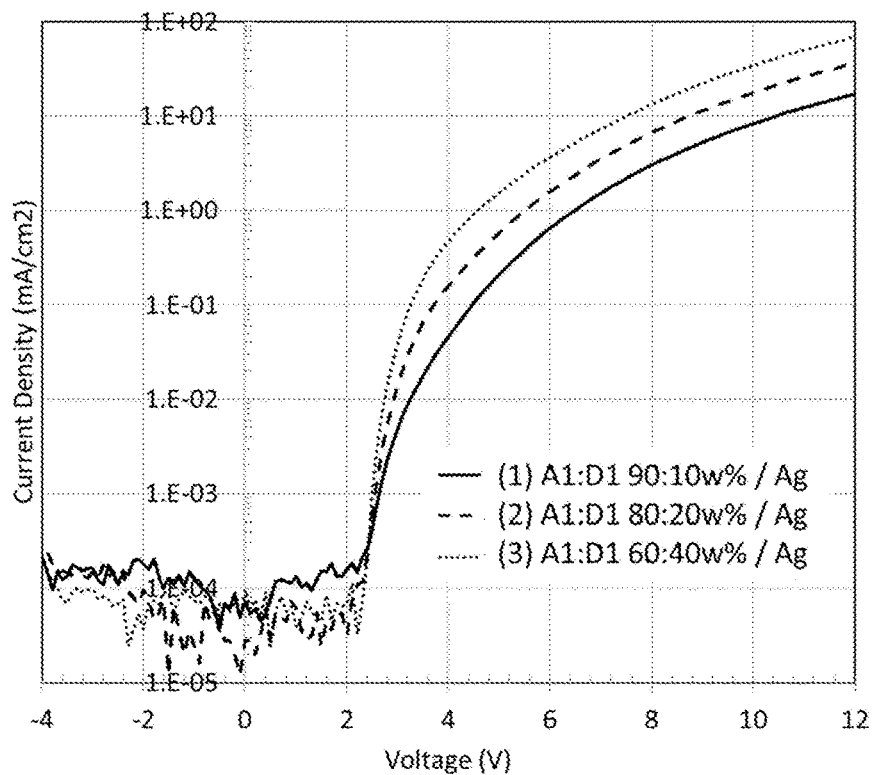
FIG. 3 is a graph of current density vs. voltage for green light emitting OLEDs according to embodiments of the invention.
Figure 4:
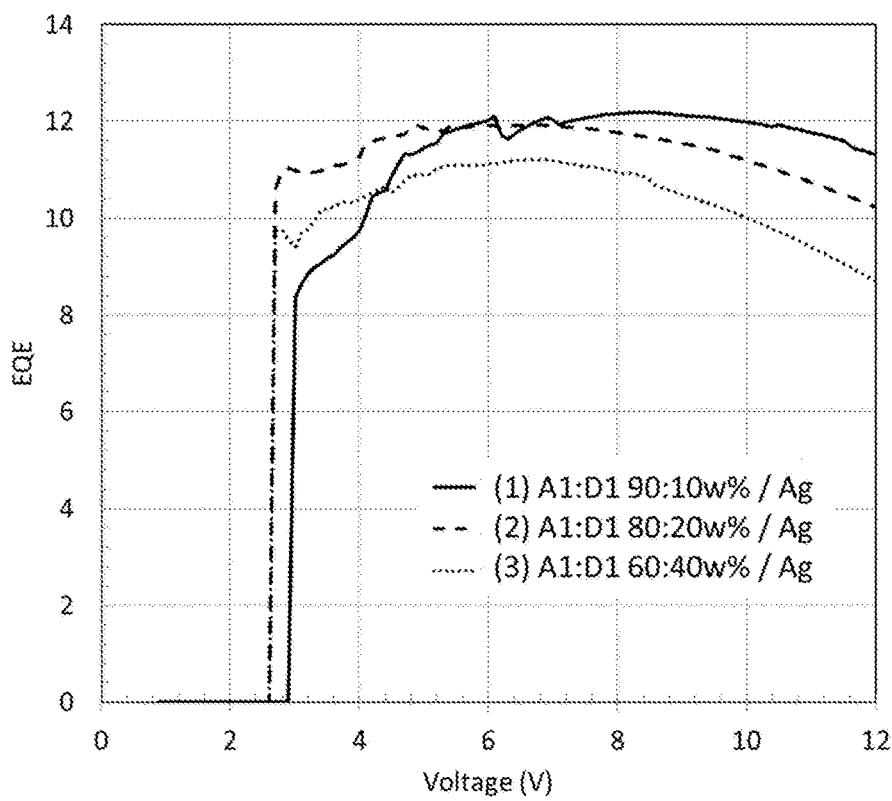
FIG. 4 is a graph of external quantum efficiency vs. voltage for green light emitting OLEDs according to embodiments of the invention.
Figure 5:
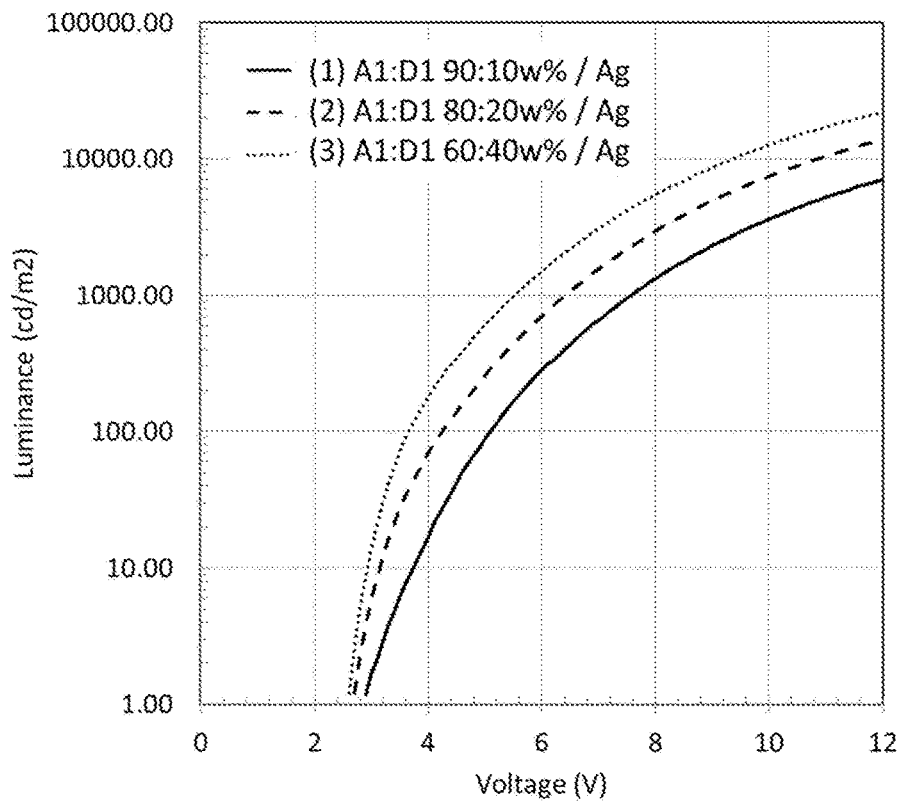
FIG. 5 is a graph of luminance vs. voltage for green light emitting OLEDs according to embodiments of the invention.
Figure 6:
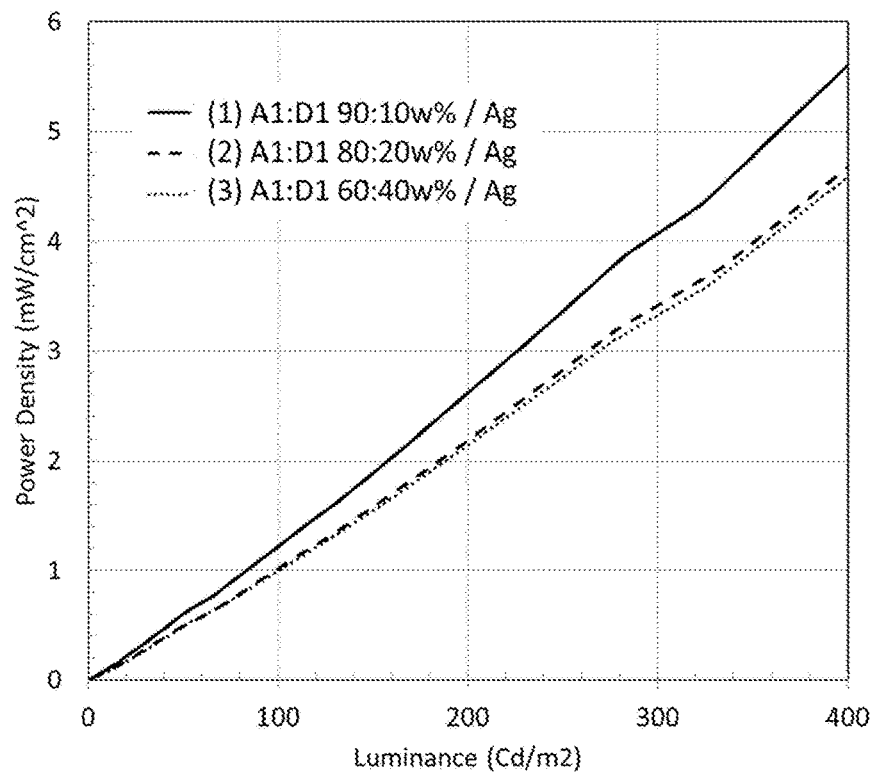
FIG. 6 is a graph of power density vs. luminance for green light emitting OLEDs according to embodiments of the invention.

With reference to FIG. 2 of the figures, in which dopant Compound Example 1 is denoted "D1" and Acceptor Polymer 1 is denoted "A1", the n-dopant concentration has very little effect on the colour of emission of the device.

With reference to FIG. 3-6, increasing the concentration of n-dopant results in an increase in device conductivity, indicating a higher degree of n-doping at higher n-dopant concentrations.

Device Example 2

White light-emitting devices having the following structure were prepared:
ITO/HIL (35 nm)/HTL (22 nm)/LEL (65 nm)/EIL (20 nm)/
 Ag (100 nm)
in which ITO is an indium tin oxide anode; HIL is a hole-injection layer; HTL is a hole-transporting layer; LEL is a light-emitting layer; and EIL is an electron injection layer.

The devices were formed as described for Device Example 1 except that a hole transporting layer was formed between HIL and LEL by spin-coating Hole-Transporting Polymer 1 from xylene solution and crosslinking the polymer by heating, and LEL was formed by spin-coating White Polymer 1 from xylene solution.

The Polymer Example 1: n-dopant 1 weight ratio was as given in Table 1. The cathode was formed by evaporation of silver.

TABLE 2

| Device | Polymer Example 1:n-dopant 1 wt:wt |
|---|---|
| Comparative Device 2A | 100:0 |
| Device Example 2A | 70:30 |
| Device Example 2B | 50:50 |

For the purpose of comparison, Comparative Device 2 was formed as described above except that no electron-injection layer was formed and the silver cathode was formed directly on the light-emitting layer.

Hole-Transporting Polymer 1 was formed by Suzuki polymerization as described in WO 00/53656 of 1,4-dialkylphenylene repeat units of formula, an amine repeat unit as described in WO 2005/049546 and 2,7-linked fluorene repeat units substituted with crosslinkable groups.

White Polymer 1 was formed by Suzuki polymerization as described in WO 00/53656 of the following monomers:

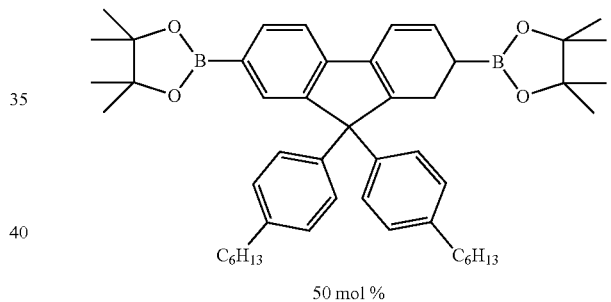

50 mol %

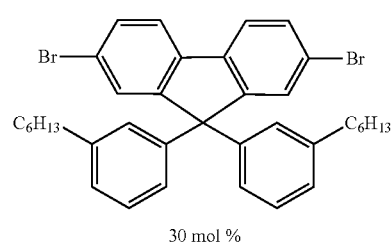

30 mol %

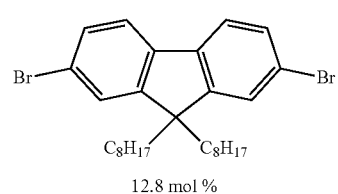

12.8 mol %

-continued

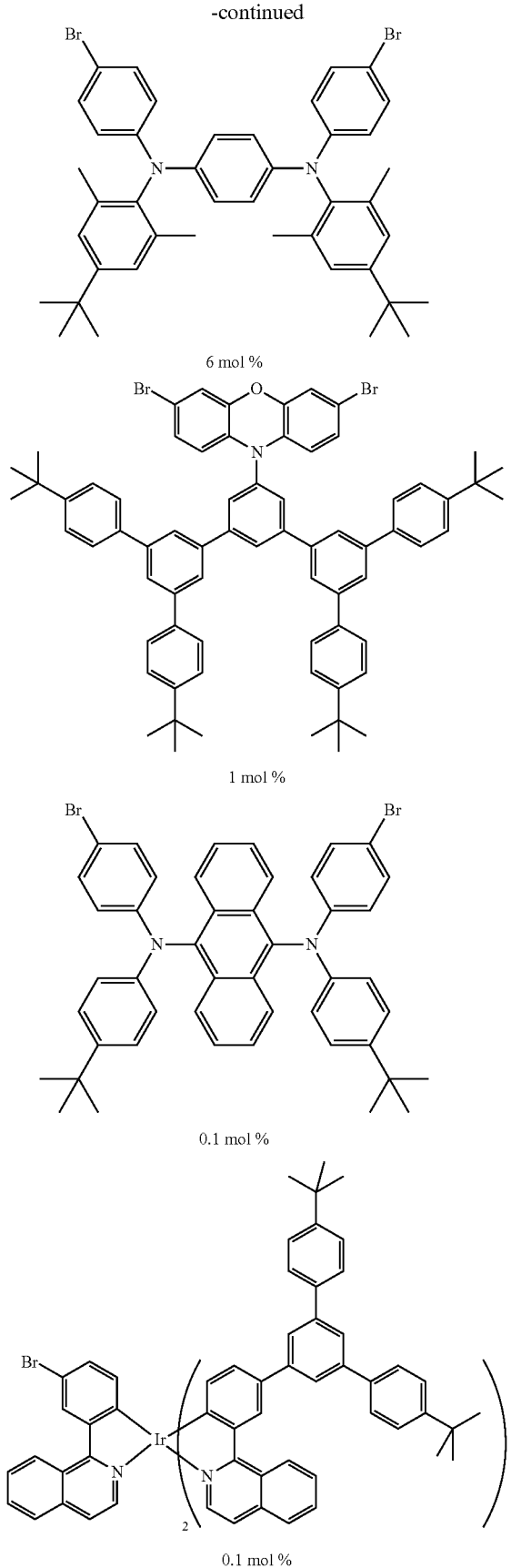

6 mol %

1 mol %

0.1 mol %

0.1 mol %

Figure 7:
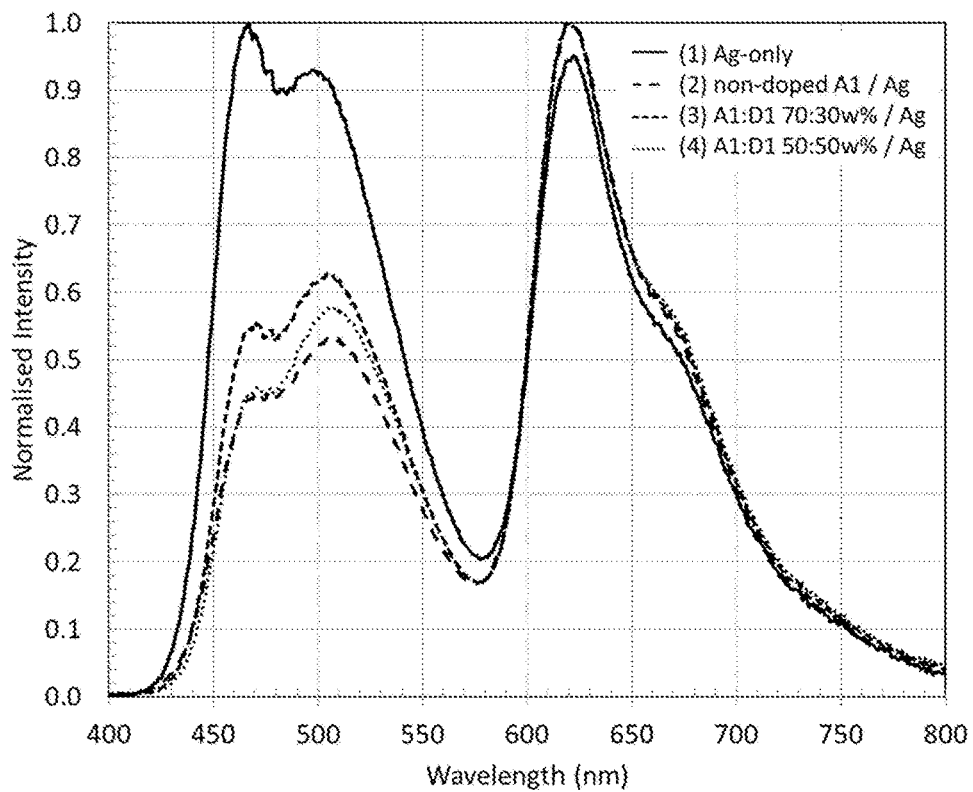
FIG. 7 shows the electroluminescent spectra for white light emitting OLEDs according to embodiments of the invention and comparative white OLEDs.

With reference to FIG. 7, the emission of Comparative Device 2 is very different from those of Device Examples 2A and 2B, indicating an effect on charge (hole and electron) balance in the light-emitting layer.

Figure 8:
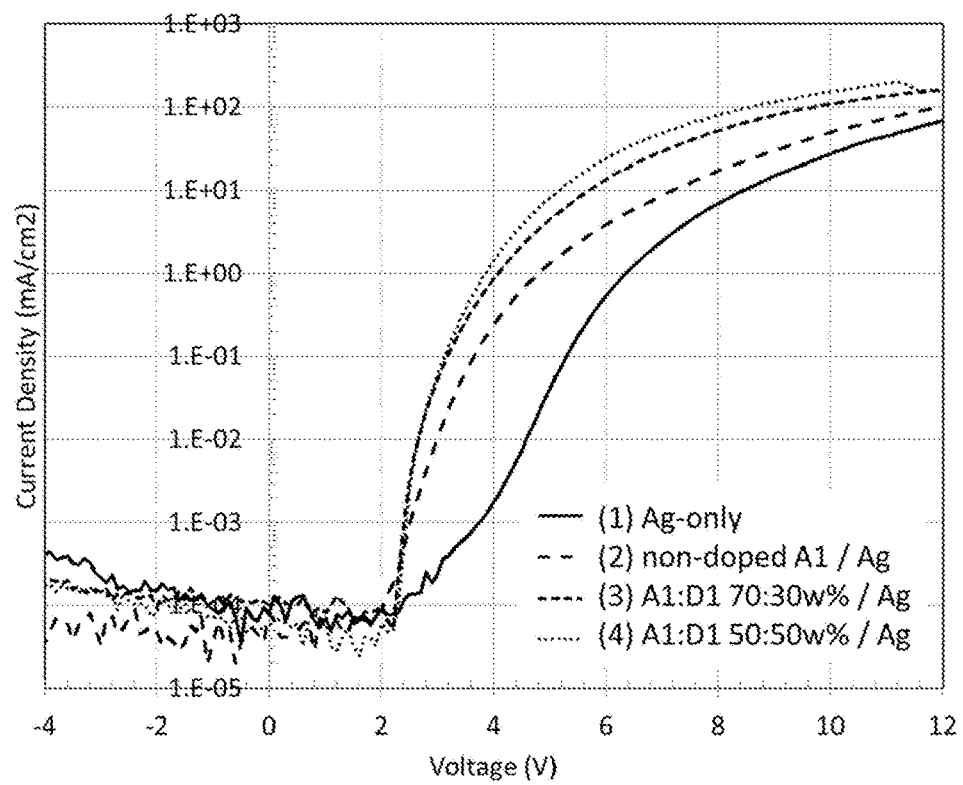
FIG. 8 is a graph of current density vs. voltage for white light emitting OLEDs according to embodiments of the invention and comparative white devices.
Figure 9:
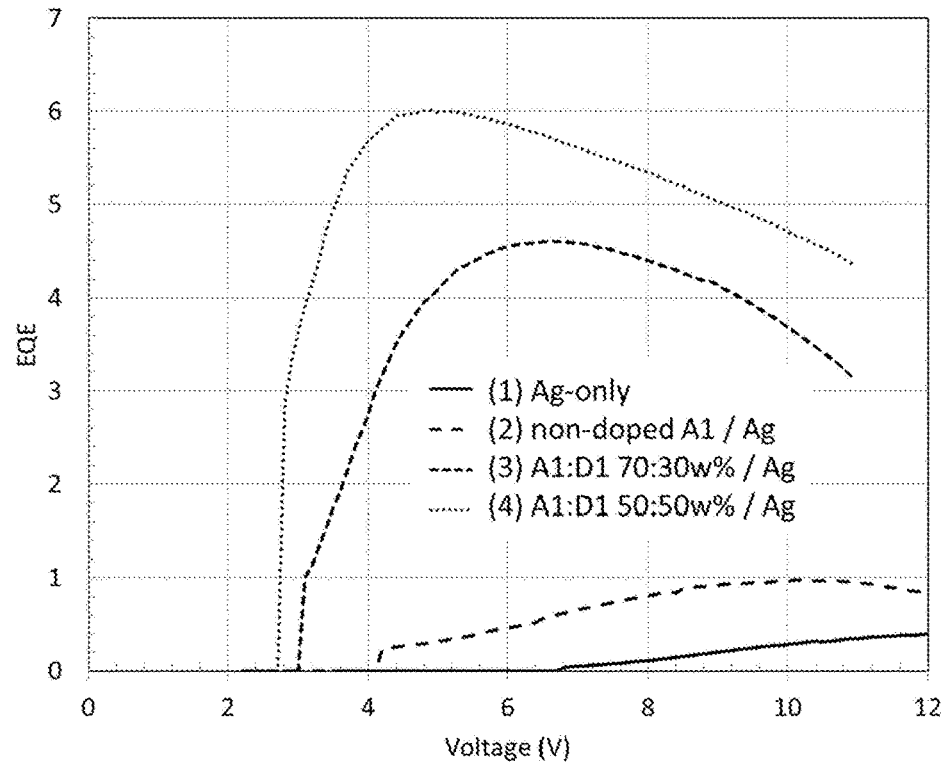
FIG. 9 is a graph of external quantum efficiency vs. voltage for white light emitting OLEDs according to embodiments of the invention and comparative white OLEDs.
Figure 10:
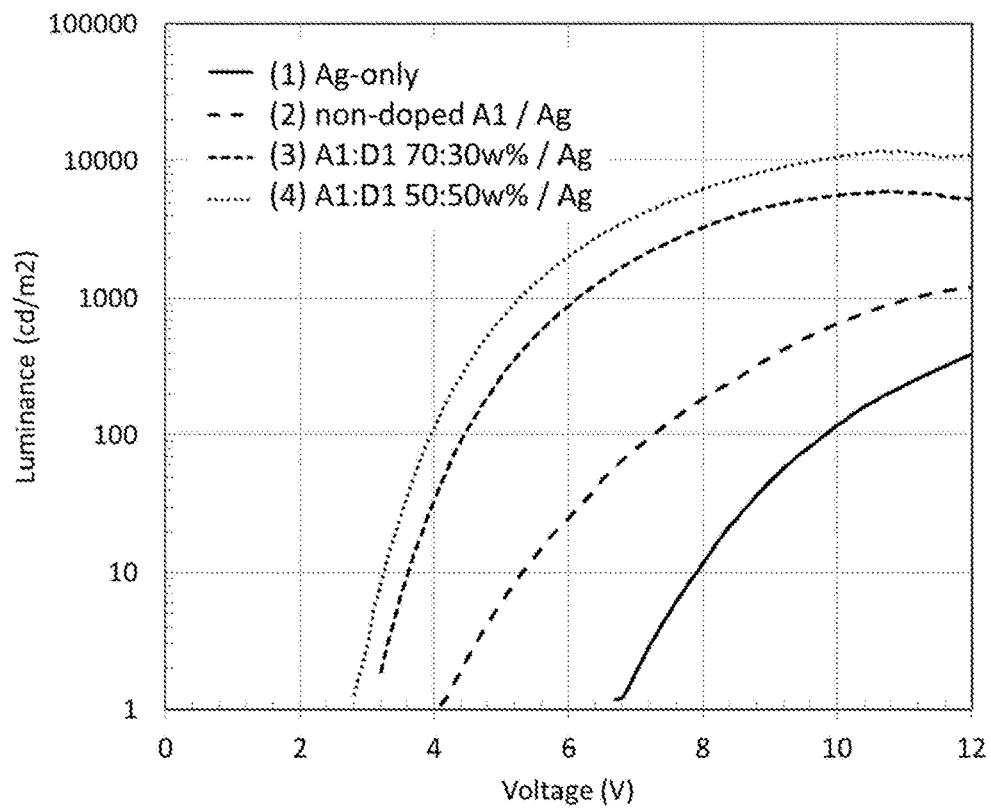
FIG. 10 is a graph of luminance vs. voltage for white light emitting OLEDs according to embodiments of the invention and comparative white OLEDs.
Figure 11:
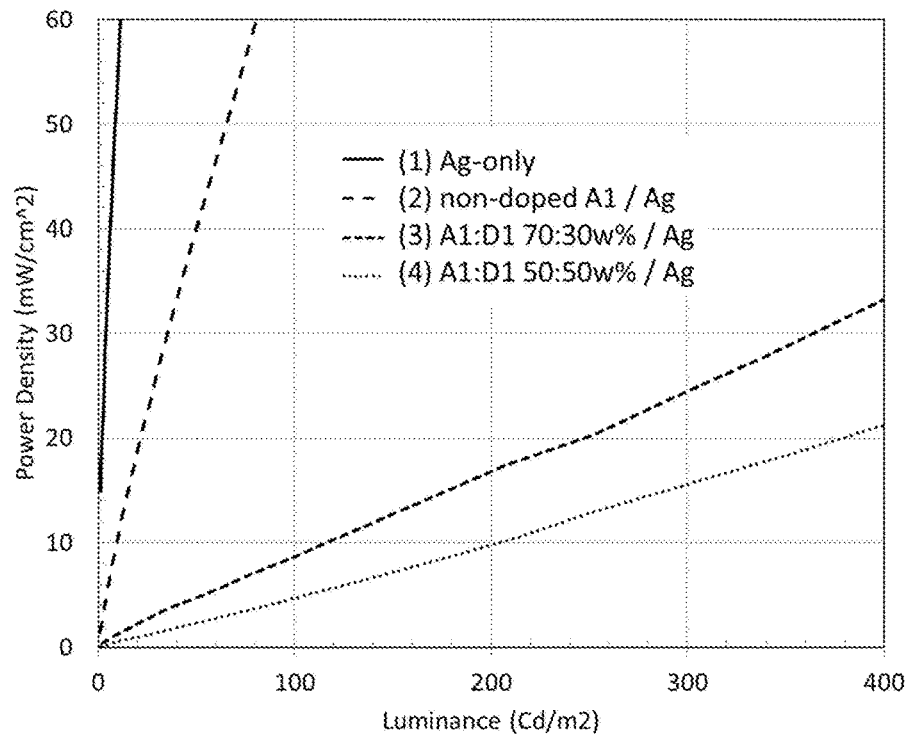
FIG. 11 is a graph of power density vs. luminance for white light emitting OLEDs according to embodiments of the invention and comparative white OLEDs.

With reference to FIGS. 8-10, Device Examples 2A and 2B give higher current density, external quantum efficiency and luminance at a given voltage than either Comparative Device 2 or 2A. With reference to FIG. 11, increasing dopant concentration reduces the power density required for achieving a given luminance.

Device Example 3

Blue light-emitting devices were formed as described for Device Example 2 except LEL was formed by spin-coating Blue Polymer 1 from xylene solution.

The Polymer Example 1: n-dopant 1 weight ratio was as given in Table 3. The cathode was formed by evaporation of silver.

TABLE 3

| Device | Polymer Example 1:n-dopant 1 wt:wt |
| --- | --- |
| Comparative Device 3 | 100:0 |
| Device Example 3A | 70:30 |
| Device Example 3B | 60:40 |
| Device Example 3C | 50:50 |

For the purpose of comparison, Comparative Device 3 was formed as described above except that no electron-injection layer was formed and the silver cathode was formed directly on the light-emitting layer.

Blue Polymer 1 is a blue fluorescent polymer comprising 2,7-linked fluorene repeat units and an amine repeat unit having the following structure formed by Suzuki polymerization as described in WO 00/53656:

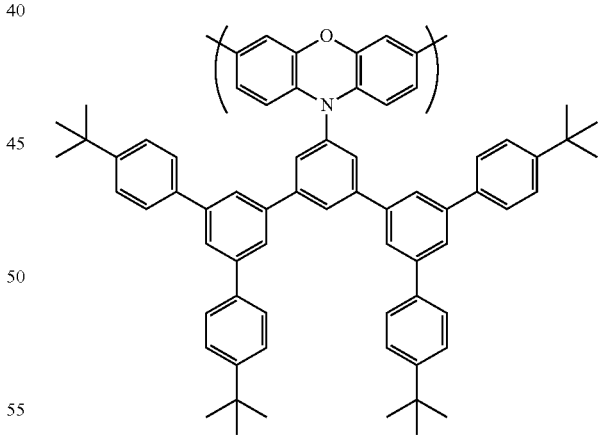

Figure 12:
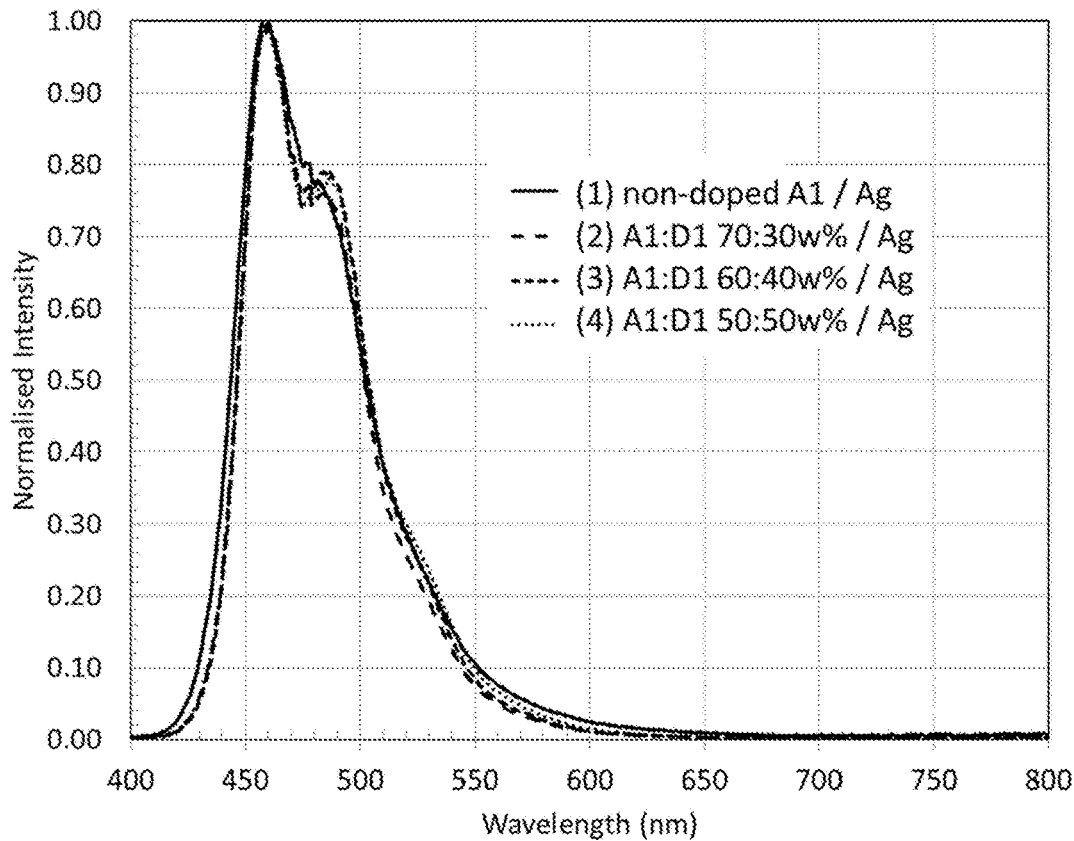
FIG. 12 shows the electroluminescent spectra for blue light emitting OLEDs according to embodiments of the invention and a comparative blue OLED.

With reference to FIG. 12, no light was observed from Comparative Device 3. Very similar spectra were obtained for all other devices.

Figure 13:
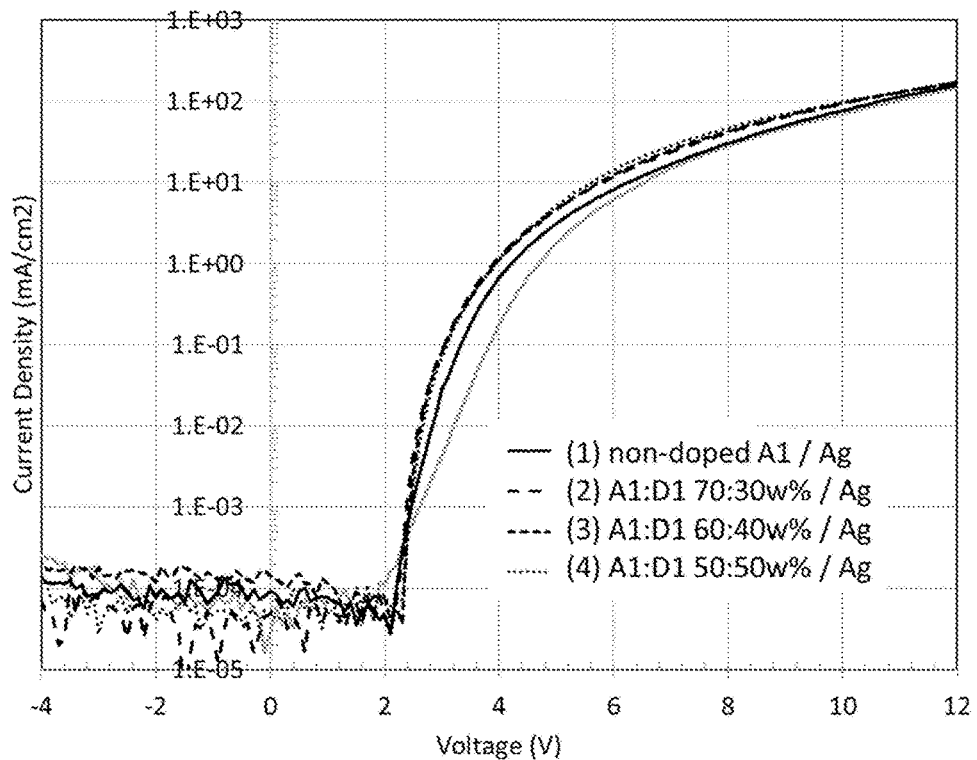
FIG. 13 is a graph of current density vs. voltage for blue light emitting OLEDs according to embodiments of the invention and a comparative blue OLED.
Figure 14:
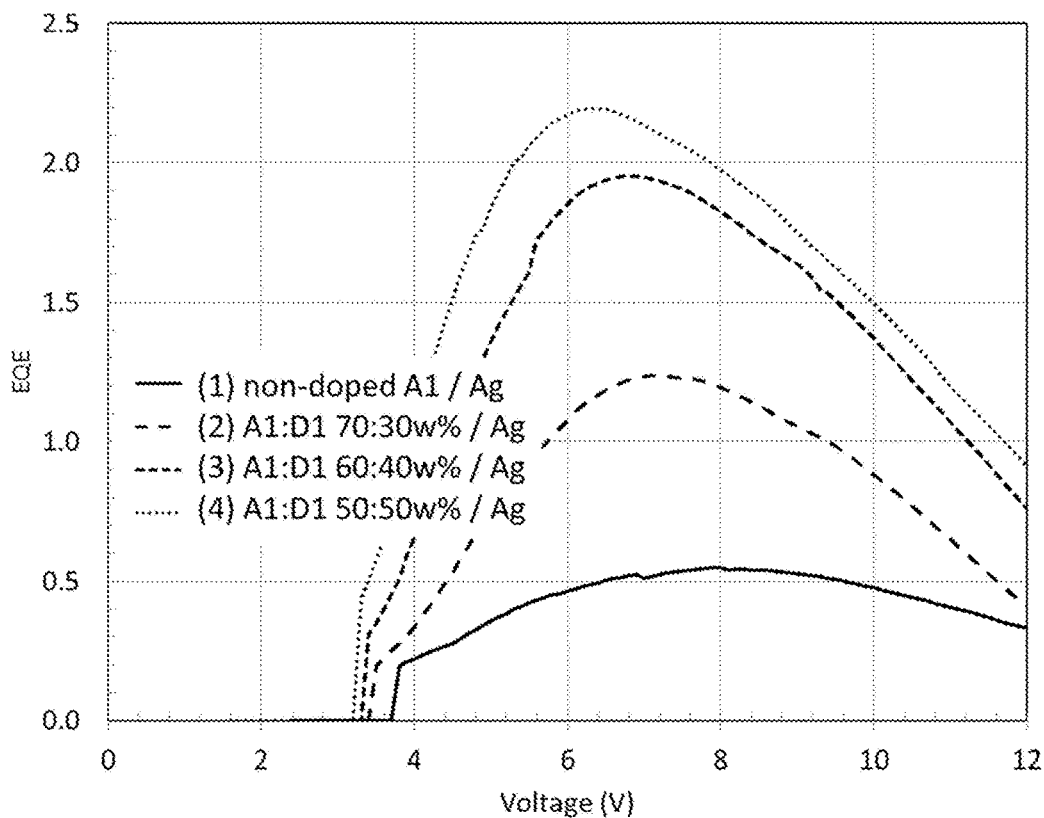
FIG. 14 is a graph of external quantum efficiency vs. voltage for blue light emitting OLEDs according to embodiments of the invention and a comparative blue OLED.
Figure 15:
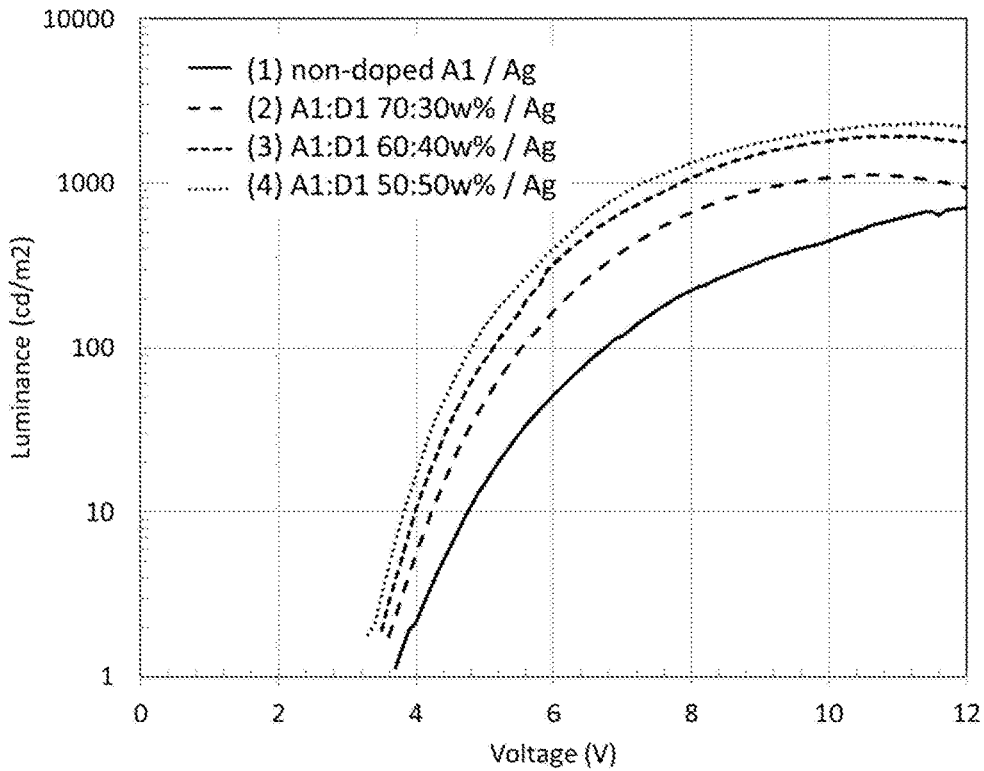
FIG. 15 is a graph of luminance vs. voltage for blue light emitting OLEDs according to embodiments of the invention and a comparative blue OLED.

With reference to FIGS. 13-15 current density, external quantum efficiency and luminance are higher at a given voltage for the exemplary devices than for the comparative devices.

Figure 16:
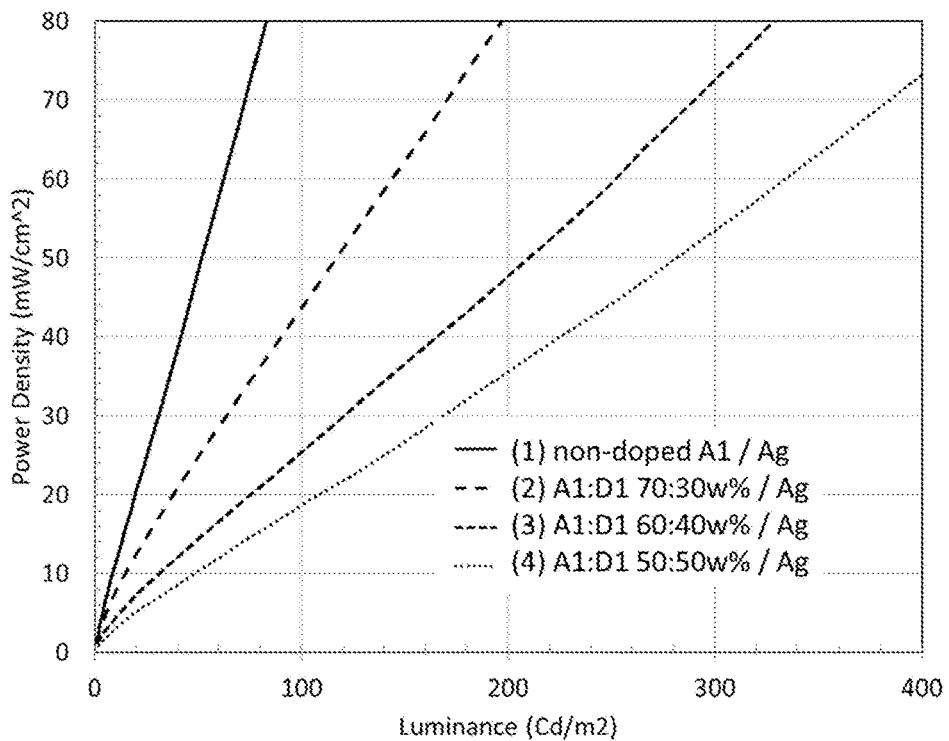
FIG. 16 is a graph of power density vs. luminance for blue light emitting OLEDs according to embodiments of the invention and a comparative blue OLED.

With reference to FIG. 16, increasing dopant concentration reduces the power density at a given luminance.

Device Example 4

A device having the following structure was prepared:

ITO/HIL (50 nm)/LEL (80 nm)/EIL (20 nm)/Ag (100 nm)

The device was formed according to the process described above.

The light-emitting layer was formed by spin-coating a composition of Host Polymer 1, and Green Phosphorescent Emitter 1, described above, from xylene solution.

The EIL was formed by spin-coating a composition of Polymer Example 1, described above (80 wt %), and NADH (20 wt %) from methanol solution:

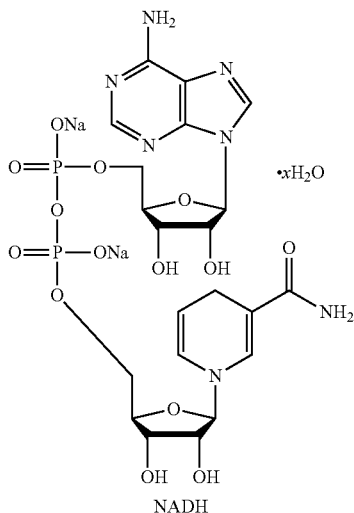

NADH

Comparative Device 4A was formed as for Device Example 4 except that no electron injection layer was formed.

Comparative Device 4B was formed as for Device Example 4 except that no NADH was included in the electron injection layer.

Figure 17:
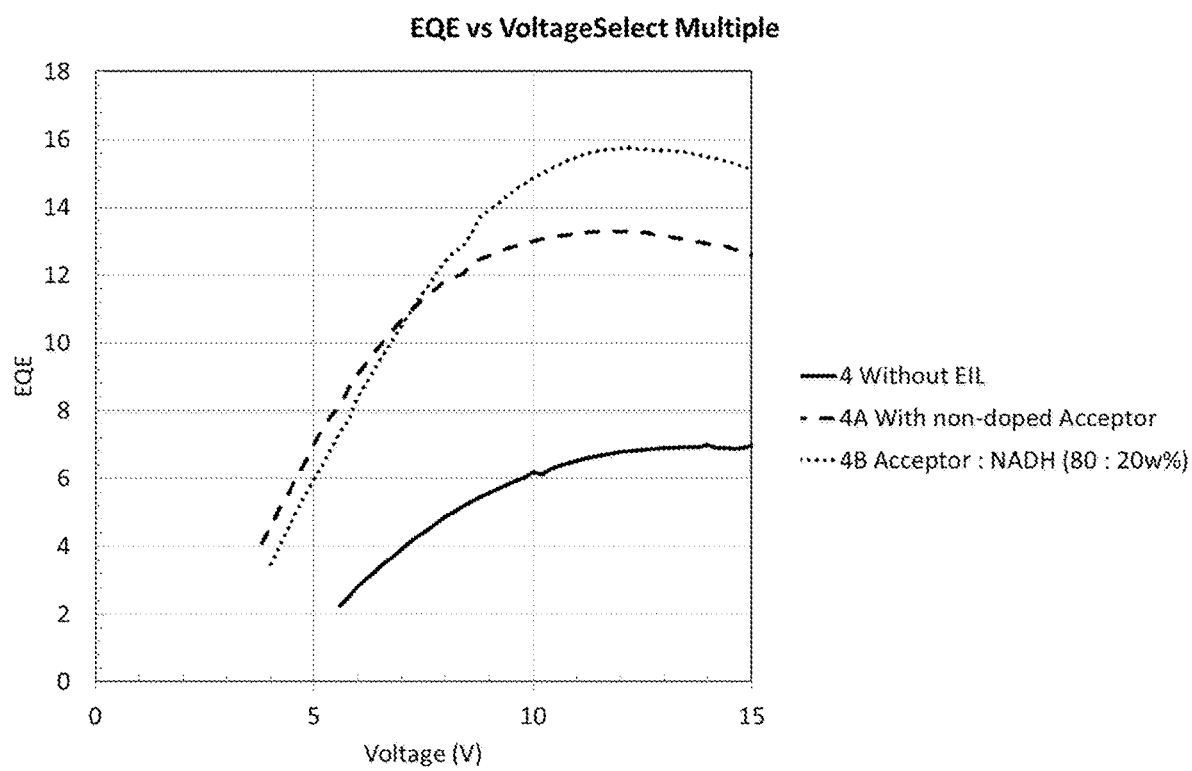
FIG. 17 is a graph of external quantum efficiency vs. voltage for a green phosphorescent OLED according to an embodiment of the invention and comparative OLEDs.

With reference to FIG. 17, Comparative Device 4A (solid line in FIG. 17), which contains no electron injection layer, has a much lower external quantum efficiency than for either Comparative Device 4B (dashed line) or Device Example 4 (dotted line), and Device Example 4 has a similar EQE at lower voltages and a significantly higher EQE at higher voltages as compared to Comparative Device 4B. A higher peak efficiency is achieved by Device Example 4 than either Comparative Device 4A or 4B.

Formation of a device having the structure of Device Example 1 in which Acceptor Polymer 1 was replaced with a polymer having no ionic substituents and which is deposited from a non-polar solution onto the light-emitting layer was not possible due to dissolution of the underlying light-emitting layer.

Although the present invention has been described in terms of specific exemplary embodiments, it will be appreciated that various modifications, alterations and/or combinations of features disclosed herein will be apparent to those skilled in the art without departing from the scope of the invention as set forth in the following claims

The invention claimed is:

1. A charge-transfer salt formed from a material comprising a repeat unit of formula (I) and an n-dopant:

wherein the n-dopant comprises 2,3-dihydro-1H-benzoimidazole; BG is a backbone group of the repeat unit; $R^1$ is an ionic substituent comprising at least one cationic or anionic group; n is at least 1; $R^2$ is a non-ionic substituent; and m is 0 or a positive integer; the material further comprising a counterion balancing the charge of the cationic or anionic group.

2. A charge-transfer salt according to claim 1 wherein BG is $Ar^1$ wherein $Ar^1$ is an arylene or heteroarylene group.

3. A charge-transfer salt according to claim 2 wherein $Ar^1$ is a $C_{6-20}$ arylene group.

4. A charge-transfer salt according to claim 3 wherein $Ar^1$ is fluorene.

5. A charge-transfer salt according to claim 4 wherein the unit of formula (I) is selected from formulae (Ia) and (Ib):

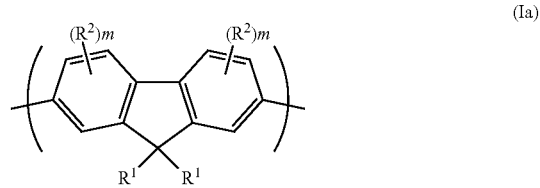

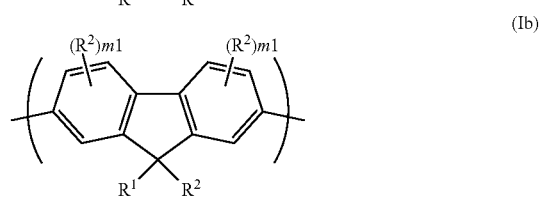

wherein m1 independently in each occurrence is 0 or a positive integer.

6. A charge-transfer salt according to claim 1 wherein $R^1$ is an anionic or cationic group.

7. A charge transfer salt according to claim 1 wherein the material comprising a repeat unit of formula (I) is a polymer.

8. A charge-transfer salt according to claim 7 wherein the polymer is a copolymer comprising a repeat unit of formula (I) and one or more co-repeat units.

9. A charge-transfer salt according to claim 7 wherein the polymer is a conjugated polymer.

10. A charge-transfer salt according to claim 8 wherein the polymer comprises a co-repeat unit of formula (III):

wherein $Ar^3$ is a $C_{6-20}$ arylene group; $R^4$ is a substituent comprising at least one cyano group; a is at least 1; $R^{17}$ is a substituent; and b is 0 or a positive integer.

11. A charge-transfer salt according to claim 8 wherein the repeat unit of formula (I) is 0.1-90 mol % of the repeat units of the polymer.

12. A charge-transfer salt according to claim 1 wherein the material comprising a repeat unit of formula (I): n-dopant weight ratio is in the range 99: 1-30:70.

13. A method of forming a charge-transfer salt according to claim 1 comprising the step of activating a composition comprising the material comprising a repeat unit of formula (I) and the n-dopant to cause the n-dopant to dope the material comprising a unit of formula (I).

14. An organic electronic device comprising a layer comprising a charge-transfer salt according to claim 1.

15. An organic electronic device according to claim 14 wherein the organic electronic device is an organic light-emitting device comprising an anode, a cathode and a light-emitting layer between the anode and the cathode and wherein the layer comprising the charge-transfer salt is an electron injection layer between the light-emitting layer and the cathode.

16. An organic electronic device according to claim 15 wherein the electron injection layer is in contact with the light-emitting layer.

17. A method of forming a device according to claim 14 comprising the step of depositing a material comprising a repeat unit of formula (I) from a polar solvent.

18. A formulation comprising a composition according to claim 17 and at least one polar solvent.

19. A method of forming a layer of an organic electronic device comprising a charge-transfer salt, the method comprising the step of depositing a formulation according to claim 18 onto a surface; evaporating the at least one solvent; and activating the n-dopant.

20. A charge-transfer salt according to claim 1 wherein the n-dopant is substituted with an ionic substituent.

21. A charge-transfer salt according to claim 1 wherein the n-dopant is a compound of formula (V):

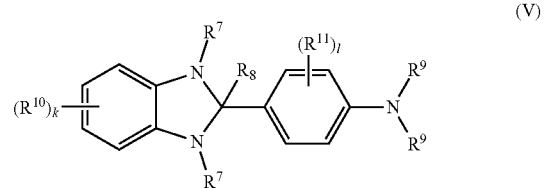

wherein:
each $R^7$ is independently a $C_{1-20}$ hydrocarbyl group;
$R^8$ is H or a $C_{1-20}$ hydrocarbyl group;
each $R^9$ is independently a $C_{1-20}$ hydrocarbyl group;
each $R^{10}$ is independently a substituent and k is 0 or a positive integer; and
each $R^{11}$ is independently a substituent and l is 0 or a positive integer.

22. A composition comprising a material comprising a repeat unit of formula (I) and an n-dopant:

wherein the n-dopant comprises 2,3-dihydro-1H-benzoimidazole; BG is a backbone group of the repeat unit; $R^1$ is an ionic substituent comprising at least one cationic or anionic group; n is at least 1; $R^2$ is a non-ionic substituent; and m is 0 or a positive integer; the material further comprising a counterion balancing the charge of the cationic or anionic group.

* * * * *